(12) United States Patent
Hinago et al.

(10) Patent No.: US 7,109,144 B2
(45) Date of Patent: Sep. 19, 2006

(54) OXIDE CATALYST FOR OXIDATION OR AMMOXIDATION

(75) Inventors: Hidenori Hinago, Kurashiki (JP); Mamoru Watanabe, Okayama-ken (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 10/011,286

(22) Filed: Dec. 11, 2001

(65) Prior Publication Data

US 2002/0115879 A1    Aug. 22, 2002

(30) Foreign Application Priority Data

Dec. 13, 2000    (JP) .............................. 2000-378530

(51) Int. Cl.
*B01J 23/22*    (2006.01)

(52) U.S. Cl. ..................................... 502/312

(58) Field of Classification Search ................ 502/312; 501/312
See application file for complete search history.

(56) References Cited

U.S. PATENT DOCUMENTS

| | | | |
|---|---|---|---|
| 5,750,760 A | 5/1998 | Ushikubo et al. | |
| 5,994,580 A | 11/1999 | Takahashi et al. | |
| 6,036,880 A * | 3/2000 | Komada et al. ............. | 502/353 |
| 6,043,185 A | 3/2000 | Cirjak et al. | |
| 6,060,422 A | 5/2000 | Takahashi et al. | |
| 6,143,916 A * | 11/2000 | Hinago et al. ............... | 558/321 |
| 6,291,393 B1 * | 9/2001 | Tu et al. ...................... | 502/311 |
| 6,346,647 B1 * | 2/2002 | Tu et al. ...................... | 562/549 |
| 6,610,629 B1 * | 8/2003 | Hinago et al. ............... | 502/300 |

FOREIGN PATENT DOCUMENTS

| | | |
|---|---|---|
| DE | 199 83 250 T1 | 8/2001 |
| JP | 9-278680 A | 10/1997 |
| JP | 9-316023 A | 12/1997 |
| JP | 10-28862 A | 2/1998 |
| JP | 10-36311 A | 2/1998 |
| JP | 10-45664 A | 2/1998 |
| JP | 10-81660 A | 3/1998 |
| JP | 10-118491 A | 5/1998 |
| JP | 10-128112 | 5/1998 |
| JP | 10-137585 A | 5/1998 |
| JP | 10-310539 A | 11/1998 |
| JP | 10-330343 A | 12/1998 |
| JP | 11-42434 A | 2/1999 |
| JP | 11-43314 | 2/1999 |
| JP | 11-57479 | 3/1999 |
| JP | 11-263745 | 9/1999 |
| JP | 11-285637 A | 10/1999 |
| JP | 11-343261 A | 12/1999 |
| JP | 11-343262 A | 12/1999 |
| JP | 2000-1464 A | 1/2000 |
| JP | 2000-51693 A | 2/2000 |
| JP | 2000-143244 A | 5/2000 |

\* cited by examiner

*Primary Examiner*—Kamal A. Saeed
*Assistant Examiner*—Rebecca Anderson
(74) *Attorney, Agent, or Firm*—Birch, Stewart, Kolasch & Birch, LLP

(57) ABSTRACT

Disclosed is an oxide catalyst for use in catalytic oxidation or ammoxidation of propane or isobutane in the gaseous phase, which comprises a composition represented by the $Mo_1V_aSb_bNb_cZ_dO_n$ (wherein: Z is at least one element selected from the group consisting of tungsten, chromium, titanium, aluminum, tantalum, zirconium, hafnium, manganese, iron, ruthenium, cobalt, rhodium, nickel, palladium, platinum, zinc, boron, indium, germanium, tin, lead, bismuth, yttrium, gallium, rare earth elements and alkaline earth metals: and a, b, c, d, and n are, respectively, the atomic ratios of V, Sb, Nb, Z and O, relative to Mo), wherein $0.1 \leq a < 0.4$, $0.1 < b \leq 0.4$, $0.01 \leq c \leq 0.3$, $0 \leq d \leq 1$, with the proviso that $a < b$, and n is a number determined by and consistent with the valence requirements of the other elements present. Also disclosed is a process for producing an unsaturated carboxylic acid or an unsaturated nitrile by using the above-mentioned oxide catalyst.

20 Claims, 2 Drawing Sheets

OXIDE CATALYST FOR OXIDATION OR AMMOXIDATION

BACKGROUND OF THE INVENTION

1. Field of the Invention

The present invention relates to an oxide catalyst for use in catalytic oxidation or ammoxidation of propane or isobutane in the gaseous phase. More particularly, the present invention is concerned with an oxide catalyst for use in catalytic oxidation or ammoxidation of propane or isobutane in the gaseous phase, which comprises, in a specific ratio, molybdenum (Mo), vanadium (V), antimony (Sb), niobium (Nb), oxygen (O) and at least one element Z selected from the group consisting of tungsten, chromium, titanium, aluminum, tantalum, zirconium, hafnium, manganese, iron, ruthenium, cobalt, rhodium, nickel, palladium, platinum, zinc, boron, indium, germanium, tin, lead, bismuth, yttrium, gallium, rare earth elements and alkaline earth metals, wherein the Sb/Mo atomic ratio (b) is larger than V/Mo atomic ratio (a), and the Sb/Mo atomic ratio (b) does not exceed 0.4. By the use of the oxide catalyst of the present invention in the oxidation or ammoxidation of propane or isobutane in the gaseous phase, (meth)acrylonitrile or (meth)acrylic acid can be produced with high selectivity and such high selectivity can be maintained for a long time, so that (meth)acrylonitrile or (meth)acrylic acid can be efficiently produced for a long time.

The present invention is also concerned with a process for producing an unsaturated carboxylic acid or an unsaturated nitrile in the presence of the abovementioned oxide catalyst.

2. Prior Art

Conventionally, there have been well known a process for producing (meth)acrylonitrile by ammoxidation of propylene or isobutylene, and a process for producing (meth)acrylic acid by oxidation of propylene or isobutylene. Recently, as substitutes for such processes for the ammoxidation or oxidation of propylene or isobutylene, attention has been attracted to a process for producing (meth)acrylonitrile or (meth)acrylic acid by a catalytic ammoxidation or oxidation in the gaseous phase, wherein propane or isobutane is used as a raw material instead of propylene or isobutylene. As catalysts for use in these processes, a number of catalysts have been proposed.

Of the catalysts proposed, especially, an oxide catalyst comprising Mo—V—Sb—Nb has been attracting attention, since such an oxide catalyst has advantages in that the catalyst comprises elements having a relatively low volatility, the catalyst can be used for a catalytic ammoxidation or oxidation in the gaseous phase at a low reaction temperature, and (meth)acrylonitrile or (meth)acrylic acid can be produced with relatively high selectivity and in relatively high yield.

Methods for producing (meth)acrylonitrile in the presence of the oxide catalyst comprising Mo—V—Sb—Nb (hereinafter, frequently referred to as an "Mo—V—Sb—Nb oxide catalyst") are disclosed in various patent documents, such as Unexamined Japanese Patent Application Laid-Open Specification Nos. 9-157241 (corresponding to U.S. Pat. No. 5,750,760 and EP 0767164 A1), 10-28862, 10-81660, 10-310539, 10-330343, 11-42434, 11-43314, 11-57479, 11-263745, 2000-1464, 2000-143244, WO 0012209 A1 (corresponding to DE 1998325 T), and U.S. Pat. No. 6,043,185.

Methods for producing (meth)acrylic acid in the presence of the Mo—V—Sb—Nb oxide catalyst are also disclosed in various patent documents, such as Unexamined Japanese Patent Application Laid-Open Specification Nos. 9-316023, 10-118491, 10-120617 (corresponding to U.S. Pat. Nos. 5,994,580 and 6,060,422), 10-137585, 11-285637, 11-343261, 2000-51693, 11-343262, 10-36311, 10-45664, 9-278680 and 10-128112.

Each of the above-mentioned Mo—V—Sb—Nb oxide catalysts, which are used for producing (meth)acrylonitrile or (meth)acrylic acid, comprises an oxide represented by the following formula (a):

$$Mo_1V_pSb_qNb_rO_m \qquad (a)$$

wherein p, q, r and m are, respectively, the atomic ratios of V, Sb, Nb and O, relative to Mo.

The above-mentioned conventional Mo—V—Sb—Nb oxide catalysts can be categorized into the following two groups:

(i) catalysts in which the V/Mo atomic ratio is equal to or larger than the Sb/Mo atomic ratio, i.e., p and q in formula (a) above satisfy the following relationship: $p \geq q$; and (ii) catalysts in which the Sb/Mo atomic ratio is larger than V/Mo atomic ratio, i.e., p and q in formula (a) above satisfy the following relationship: $p < q$, wherein the Sb/Mo atomic ratio is equal to or larger than 0.5, i.e., q in formula (a) above satisfies the following relationship: $q \geq 0.5$.

When the conventional Mo—V—Sb—Nb oxide catalysts mentioned above are used, (meth)acrylonitrile or (meth)acrylic acid is sometimes produced with a relatively high selectivity (hereinafter, (meth)-acrylonitrile or (meth)acrylic acid is frequently referred to as the "desired product"). However, the selectivity for the desired product, which is achieved by such conventional catalysts, is not satisfactory.

Of the Mo—V—Sb—Nb oxide catalysts of group (i) above, oxide catalysts capable of achieving a relatively high selectivity for the desired product exhibits a disadvantageously low stability. Specifically, especially when the catalytic oxidation or ammoxidation in the gaseous phase is performed in the presence of each of such oxide catalysts in a recycling mode using a gaseous feedstock mixture having a high partial pressure of propane, the selectivity for the desired product decreases with the lapse of time.

In an attempt to improve the stability of the Mo—V—Sb—Nb oxide catalysts of group (i) above so as to maintain the selectivity for the desired product at a high level, the following two methods have been proposed:

a first method in which, using a reactor having a zone in which a gaseous mixture having a higher oxygen concentration than that of a gaseous reaction mixture produced is contacted with the oxide catalyst, the oxide catalyst is continuously oxidized to regenerate the oxide catalyst (see Unexamined Japanese Patent Application Laid-Open Specification No. 11-263745); and a second method in which an Mo—V—Sb—Nb oxide catalyst of group (i) above produced by a process comprising preparing a raw material liquid mixture for the catalyst, followed by spray-drying and calcination is mixed with an aqueous solution containing Mo and Co to obtain an aqueous mixture, and the obtained aqueous mixture is spray-dried and calcined to thereby obtain a modified catalyst containing a large amount of an Mo—Co composite oxide (see Unexamined Japanese Patent Application Laid-Open Specification No. 11-57479).

Of the above-mentioned two methods, the first method is disadvantageous in that the process for the catalytic ammoxidation or oxidation in the gaseous phase inevitably becomes cumbersome. On the other hand, the second method is also disadvantageous not only in that the process for producing the oxide catalyst becomes too cumbersome, but also in that, even when silica is used to increase the strength of the catalyst, since the oxide catalyst produced in the second method contains a large amount of an Mo—Co composite oxide, it is difficult to cause the oxide catalyst to contain a satisfactory amount of silica which is needed to satisfactorily increase the strength of the oxide catalyst. Therefore, especially, it is difficult to apply the second method to the production of an oxide catalyst which is used for a reaction in a fluidized bed and, hence, is required to have a high strength.

With respect to the Mo—V—Sb—Nb oxide catalysts of group (ii) above, these catalysts have a disadvantage in that the selectivity for the desired product is low.

From the above, it is apparent that, by the conventional Mo—V—Sb—Nb oxide catalysts for the catalytic ammoxidation or oxidation, it is difficult to stably produce the desired compound with high selectivity for a long time.

SUMMARY OF THE INVENTION

In this situation, the present inventors have made extensive and intensive studies toward developing an Mo—V—Sb—Nb oxide catalyst which can be used for stably producing (meth)acrylonitrile or (meth)acrylic acid with high selectivity for a long time. As a result, it has unexpectedly been found that, by the use of a Mo—V—Sb—Nb oxide catalyst having a specific composition in the oxidation or ammoxidation of propane or isobutane in the gaseous phase, (meth)acrylonitrile or (meth)acrylic acid can be produced with high selectivity and such high selectivity can be maintained for a long time. The above-mentioned Mo—V—Sb—Nb oxide catalyst having a specific composition comprises, in a specific ratio, molybdenum (Mo), vanadium (V), antimony (Sb), niobium (Nb), oxygen (O) and at least one element Z selected from the group consisting of tungsten, chromium, titanium, aluminum, tantalum, zirconium, hafnium, manganese, iron, ruthenium, cobalt, rhodium, nickel, palladium, platinum, zinc, boron, indium, germanium, tin, lead, bismuth, yttrium, gallium, rare earth elements and alkaline earth metals, wherein the Sb/Mo atomic ratio (b) is larger than V/Mo atomic ratio (a), and the Sb/Mo atomic ratio (b) does not exceed 0.4. Based on these novel findings, the present invention has been completed.

Accordingly, it is a primary object of the present invention to provide an Mo—V—Sb—Nb oxide catalyst which can be advantageously used for stably producing (meth)acrylonitrile or (meth)acrylic acid with high selectivity for a long time.

Another object of the present invention is to provide a process for producing (meth)acrylonitrile, which comprises performing ammoxidation in the presence of the abovementioned oxide catalyst, and a process for producing (meth)acrylic acid, which comprises performing oxidation in the presence of the abovementioned oxide catalyst.

The foregoing and other objects, features and advantages of the present invention will be apparent from the following detailed description and appended claims taken in connection with the accompanying drawings.

Figure 1:
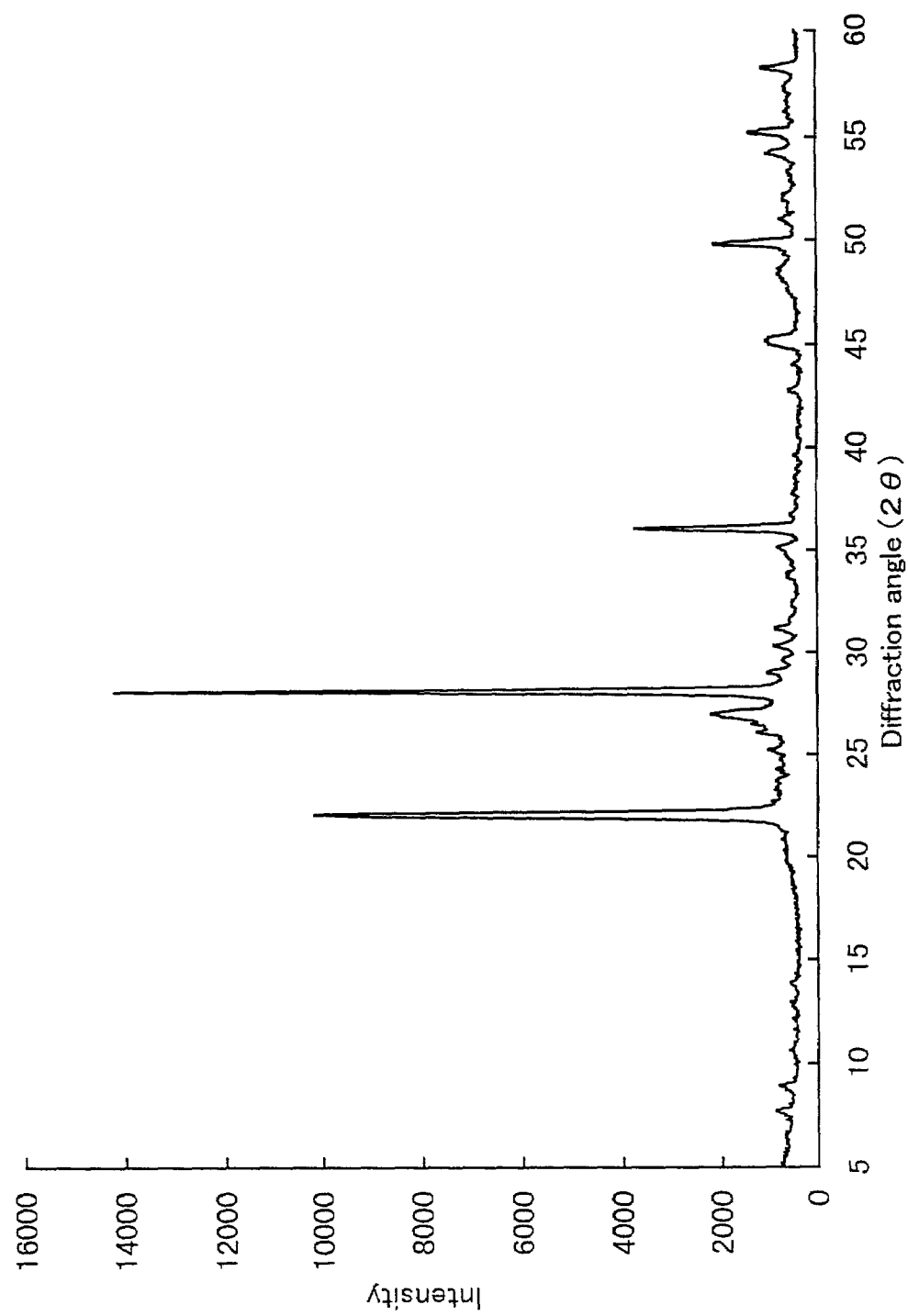
FIG. 1 is an X-ray diffraction pattern of the oxide catalyst obtained in Example 1.

DESCRIPTION OF REFERENCE NUMERALS $A_1$: Apex of the peak observed at diffraction angle (2θ) of 27.1±0.3° in an X-ray diffraction pattern of the oxide catalyst obtained using $CuK_\alpha$ as a source of X-ray;

$A_2$: Apex of the peak observed at diffraction angle (2θ) of 28.1±0.3° in an X-ray diffraction pattern of the oxide catalyst obtained using $CuK_\alpha$ as a source of X-ray;

$B_1$: Point at which the curved line of the X-ray diffraction pattern exhibits a minimum intensity value in the diffraction angle (2θ) range of 26.4±0.3°;

$B_2$: Point at which the curved line of the X-ray diffraction pattern exhibits a minimum intensity value in the diffraction angle (2θ) range of 27.6±0.3°;

$B_3$: Point at which the curved line of the X-ray diffraction pattern exhibits a minimum intensity value in the diffraction angle (2θ) range of 28.8±0.3°;

$C_1$: Point at which a straight line drawn downwardly from peak apex $A_1$ vertically to the 2θ-axis intersects with a straight line connecting points $B_1$ and $B_2$; and $C_2$: Point at which a straight line drawn downwardly from peak apex $A_2$ vertically to the 2θ-axis intersects with a straight line connecting points $B_2$ and $B_3$.

DETAILED DESCRIPTION OF THE INVENTION

According to the present invention, there is provided an oxide catalyst for use in catalytic oxidation or ammoxidation of propane or isobutane in the gaseous phase, which comprises a composition represented by the following formula (I):

$$Mo_1V_aSb_bNb_cZ_dO_n \qquad (I)$$

wherein:

Z is at least one element selected from the group consisting of tungsten, chromium, titanium, aluminum, tantalum, zirconium, hafnium, manganese, iron, ruthenium, cobalt, rhodium, nickel, palladium, platinum, zinc, boron, indium, germanium, tin, lead, bismuth, yttrium, gallium, rare earth elements and alkaline earth metals; and a, b, c, d, and n are, respectively, the atomic ratios of vanadium (V), antimony (Sb), niobium (Nb), Z and oxygen (O), relative to molybdenum (Mo), wherein:

0.1≦a<0.4, 0.1<b≦0.4, 0.01≦c≦0.3,

0≦d≦1, with the proviso that a<b, and n is a number determined by and consistent with the valence requirements of the other elements present.

For easy understanding of the present invention, the essential features and various preferred embodiments of the present invention are enumerated below.

1. An oxide catalyst for use in catalytic oxidation or ammoxidation of propane or isobutane in the gaseous phase, which comprises a composition represented by the following formula (I):

$$Mo_1V_aSb_bNb_cZ_dO_n \qquad (I)$$

wherein:
Z is at least one element selected from the group consisting of tungsten, chromium, titanium, aluminum, tantalum, zirconium, hafnium, manganese, iron, ruthenium, cobalt, rhodium, nickel, palladium, platinum, zinc, boron, indium, germanium, tin, lead, bismuth, yttrium, gallium, rare earth elements and alkaline earth metals; and a, b, c, d, and n are, respectively, the atomic ratios of vanadium (V), antimony (Sb), niobium (Nb), Z and oxygen (O), relative to molybdenum (Mo),
wherein:
$0.1 \leq a < 0.4$,
$0.1 < b \leq 0.4$,
$0.01 \leq c \leq 0.3$,
$0 \leq d \leq 1$,
with the proviso that a<b, and n is a number determined by and consistent with the valence requirements of the other elements present.

2. The oxide catalyst according to item 1 above, wherein a in formula (I) satisfies the following relationship: $0.1 \leq a \leq 0.3$.

3. The oxide catalyst according to item 1 above, wherein b in formula (I) satisfies the following relationship: $0.1 < b \leq 0.35$.

4. The oxide catalyst according to item 1 above, wherein c in formula (I) satisfies the following relationship: $0.05 \leq c \leq 0.2$.

5. The oxide catalyst according to item 1 above, wherein a in formula (I) satisfies the following relationship: $0.15 \leq a \leq 0.28$.

6. The oxide catalyst according to item 1 above, wherein b in formula (I) satisfies the following relationship: $0.2 \leq b \leq 0.33$.

7. The oxide catalyst according to item 1 above, wherein c in formula (I) satisfies the following relationship: $0.05 \leq c \leq 0.15$.

8. The oxide catalyst according to item 1 above, wherein a, b and c in formula (I) satisfy the following relationships:
$0.15 \leq a \leq 0.28$;
$0.2 \leq b \leq 0.33$;
$0.05 \leq c \leq 0.15$;
$0.5 \leq a+b+c \leq 0.69$;

$$\frac{a}{a+b+c} \geq 0.23; \text{ and}$$

$$0.59 - \frac{0.528a}{a+b+c} \leq \frac{b}{a+b+c} \leq 0.7 - \frac{0.524a}{a+b+c}.$$

9. The oxide catalyst according to item 1 above, wherein a, b and c in formula (I) satisfy the following relationships:
$0.16 \leq a \leq 0.28$;
$0.24 \leq b \leq 0.33$;
$0.07 \leq c \leq 0.15$;
$0.53 \leq a+b+c \leq 0.67$;

$$\frac{a}{a+b+c} \geq 0.26; \text{ and}$$

$$0.63 - \frac{0.549a}{a+b+c} \leq \frac{b}{a+b+c} \leq 0.68 - \frac{0.529a}{a+b+c}.$$

10. The oxide catalyst according to item 1 above, wherein a, b and c in formula (I) satisfy the following relationships:
$0.16 \leq a \leq 0.26$;
$0.24 \leq b \leq 0.30$;
$0.08 \leq c \leq 0.12$;
$0.57 \leq a+b+c \leq 0.60$;

$$\frac{a}{a+b+c} \geq 0.28; \text{ and}$$

$$0.67 - \frac{0.5975a}{a+b+c} \leq \frac{b}{a+b+c} \leq 0.67 - \frac{0.5352a}{a+b+c}.$$

11. The oxide catalyst according to item 1 above, which exhibits, in an X-ray diffraction pattern thereof obtained using $CuK_\alpha$ as a source of X-ray, peaks at diffraction angles (2θ) of:
22.1±0.3°, 28.1±0.3°, 36.1±0.3° and 45.2±0.3°;
7.8±0.3°, 8.9±0.3°, 22.1±0.3°, 27.1±0.3°, 35.2±0.3° and 45.2±0.3°; or
7.8±0.3°, 8.9±0.3°, 22.1±0.3°, 27.1±0.3°, 28.1±0.3°, 35.2±0.3°, 36.1±0.3° and 45.2±0.3°.

12. The oxide catalyst according to item 1 above, which further comprises a silica carrier having supported thereon the oxide catalyst, wherein the silica carrier is present in an amount of from 20 to 60% by weight in terms of $SiO_2$, based on the total weight of the oxide catalyst and the silica carrier in terms of $SiO_2$.

13. The oxide catalyst according to item 1 above, wherein Z in formula (I) is at least one element selected from the group consisting of tungsten, chromium, titanium, aluminum, tantalum, zirconium, iron, boron, indium, germanium and tin.

14. The oxide catalyst according to item 1 above, which is produced by a method comprising providing an aqueous raw material mixture containing compounds of molybdenum, vanadium, antimony, niobium and optionally Z, and drying the aqueous raw material mixture, followed by calcination.

15. The oxide catalyst according to item 14 above, wherein the calcination is performed at 500 to 700° C. in an atmosphere of inert gas which is substantially free of molecular oxygen.

16. The oxide catalyst according to item 14 above, wherein the aqueous raw material mixture further contains oxalic acid, wherein the molar ratio of the oxalic acid to the niobium compound in terms of niobium is in the range of from 1 to 10.

17. A process for producing acrylonitrile or methacrylonitrile, which comprises reacting propane or isobutane with ammonia and molecular oxygen in the gaseous phase in the presence of the oxide catalyst of item 1 above.

18. A process for producing acrylic acid or methacrylic acid, which comprises reacting propane or isobutane with molecular oxygen in the gaseous phase in the presence of the oxide catalyst of item 1 above.

Hereinbelow, the present invention is described in detail.

The oxide catalyst of the present invention is for use in catalytic oxidation or ammoxidation of propane or isobutane in the gaseous phase, and comprises a composition represented by the following formula (I):

$$Mo_1V_aSb_bNb_cZ_dO_n \qquad (I).$$

In formula (I), Z is at least one element selected from the group consisting of tungsten, chromium, titanium, aluminum, tantalum, zirconium, hafnium, manganese, iron, ruthenium, cobalt, rhodium, nickel, palladium, platinum, zinc, boron, indium, germanium, tin, lead, bismuth, yttrium, gallium, rare earth elements and alkaline earth metals.

It is preferred that Z is at least one element selected from the group consisting of tungsten, chromium, titanium, aluminum, tantalum, zirconium, iron, boron, indium, germanium and tin. It is more preferred that Z is at least one element selected from the group consisting of tungsten, titanium, aluminum, iron and boron.

In formula (I), a, b, c, d and n are, respectively, the atomic ratios of vanadium (V), antimony (Sb), niobium (Nb), Z and oxygen (O), relative to molybdenum (Mo). Atomic ratios a, b, c and d are determined by the charging ratios of the below-described raw material compounds used for producing the oxide catalyst of the present invention.

In formula (I), a satisfies the relationship: $0.1 \leq a < 0.4$, preferably $0.1 \leq a \leq 0.3$, more preferably $0.15 \leq a \leq 0.28$. When $a < 0.1$ or $a \geq 0.4$, the selectivity for (meth)acrylonitrile or (meth)acrylic acid is disadvantageously low, or decreases with the lapse of time during the reaction.

In formula (I), b satisfies the relationship: $0.1 < b \leq 0.4$, preferably $0.1 < b \leq 0.35$, more preferably $0.2 \leq b \leq 0.33$. When $b \leq 0.1$ or $b > 0.4$, the selectivity for (meth)acrylonitrile or (meth)acrylic acid is disadvantageously low, or decreases with the lapse of time during the reaction.

In formula (I), c satisfies the relationship: $0.01 \leq c \leq 0.3$, preferably $0.05 \leq c \leq 0.2$, more preferably $0.05 \leq c \leq 0.15$. When $c < 0.01$ or $c > 0.3$, the selectivity for (meth)acrylonitrile or (meth)acrylic acid is disadvantageously low, or decreases with the lapse of time during the reaction.

In formula (I), d satisfies $0 \leq d \leq 1$, preferably $0 \leq d \leq 0.4$, more preferably $0.01 \leq d \leq 0.1$.

When Al is used as Z element, it is preferred that d satisfies the relationship: $0 \leq d \leq 0.1$, more advantageously $0.01 \leq d \leq 0.05$.

In formula (I), a and b satisfy the relationship: $a < b$. When $a \geq b$, the selectivity for (meth)acrylonitrile or (meth)acrylic acid is disadvantageously low, or decreases with the lapse of time during the reaction.

In formula (I), n is a number determined by and consistent with the valence requirements of the other elements present.

In an especially preferred embodiment of the present invention, a, b and c are within their respective more preferred ranges mentioned above. Specifically, in the especially preferred embodiment of the present invention, a, b and c in formula (I) satisfy the following relationships:
$0.15 \leq a \leq 0.28$;
$0.2 \leq b \leq 0.33$; and
$0.05 \leq c \leq 0.15$.

Further, in the especially preferred embodiment of the present invention, it is preferred that a, b and c not only are within their respective more preferred ranges mentioned above, but also satisfy specific relationships. Specifically, it is preferred that a, b and c in formula (I) satisfy the following relationships:
$0.15 \leq a \leq 0.28$;
$0.2 \leq b \leq 0.33$;
$0.05 \leq c \leq 0.15$;
$0.5 \leq a+b+c \leq 0.69$;

$$\frac{a}{a+b+c} \geq 0.23; \text{ and}$$

$$0.59 - \frac{0.528a}{a+b+c} \leq \frac{b}{a+b+c} \leq 0.7 - \frac{0.524a}{a+b+c}.$$

It is more preferred that a, b and c in formula (I) satisfy the following relationships:
$0.16 \leq a \leq 0.28$;
$0.24 \leq b \leq 0.33$;
$0.07 \leq c \leq 0.15$;
$0.53 \leq a+b+c \leq 0.67$;

$$\frac{a}{a+b+c} \geq 0.26; \text{ and}$$

$$0.63 - \frac{0.549a}{a+b+c} \leq \frac{b}{a+b+c} \leq 0.68 - \frac{0.529a}{a+b+c}.$$

It is still more preferred that a, b and c in formula (I) satisfy the following relationships:
$0.16 \leq a \leq 0.26$;
$0.24 \leq b \leq 0.30$;
$0.08 \leq c \leq 0.12$;
$0.57 \leq a+b+c \leq 0.60$;

$$\frac{a}{a+b+c} \geq 0.28; \text{ and}$$

$$0.67 - \frac{0.5975a}{a+b+c} \leq \frac{b}{a+b+c} \leq 0.67 - \frac{0.5352a}{a+b+c}.$$

It is preferred that the oxide catalyst of the present invention exhibits, in an X-ray diffraction pattern thereof obtained using $CuK_\alpha$ as a source of X-ray, peaks at diffraction angles (2θ) of:
22.1±0.3°, 28.1±0.3°, 36.1±0.3° and 45.2±0.3°;
7.8±0.3°, 8.9±0.3°, 22.1±0.3°, 27.1±0.3°, 35.2±0.3° and 45.2±0.3°; or
7.8±0.3°, 8.9 ±0.3°, 22.1±0.3°, 27.1±0.3°, 28.1±0.3°, 35.2±0.3°, 36.1±0.3° and 45.2±0.3°.

It is especially preferred that the oxide catalyst of the present invention exhibits, in an X-ray diffraction pattern thereof obtained using $CuK_\alpha$ as a source of X-ray, peaks at diffraction angles (2θ) of 7.8±0.3°, 8.9±0.3°, 22.1±0.3°, 27.1±0.3°, 28.1±0.3°, 35.2±0.3°, 36.1±0.3° and 45.2±0.3°.

In the present invention, the X-ray diffraction (XRD) analysis is conducted under the following conditions:

| | |
|---|---|
| Tube voltage | 40 kV |
| Tube current | 190 mA |
| Divergence slit | 1° |
| Scatter slit | 1° |
| Receiving slit | 0.3 mm |
| Scanning speed | 5°/min. |
| Sampling interval | 0.02° |

The oxide catalyst which exhibits, in an X-ray diffraction (XRD) pattern thereof, peaks at the abovementioned diffraction angles advantageously exhibits a high catalytic activity and a high selectivity for the desired compound. The reason why such an oxide catalyst exhibits a high catalytic activity and a high selectivity for the desired compound has not yet been elucidated. However, it is presumed that such an oxide catalyst contains an oxide which exhibits, in an XRD pattern thereof obtained using $CuK_\alpha$ as a source of X-ray, peaks at diffraction angles (2θ) of 22.1±0.3°, 28.1±0.3°, 36.1±0.3° and 45.2±0.3°; and/or an oxide which exhibits, in an XRD thereof obtained using $CuK_\alpha$ as a source of X-ray, peaks at diffraction angles (2θ) of 7.8±0.3°, 8.9±0.3°, 22.1±0.3°, 27.1±0.3°, 35.2±0.3° and 45.2±0.3°; and that such an oxide or oxides contribute to the improvement of the performance of the oxide catalyst.

The oxide catalyst of the present invention may exhibit, in the XRD pattern thereof, in addition to the above-mentioned peaks, a peak having a high intensity, as long as the performance of the oxide catalyst is not harmfully affected.

Hereinafter, a peak appearing at a certain diffraction angle (2θ) of x±0.3° is designated as "$P^x$" (for example, a peak appearing at diffraction angle (2θ) of 7.8±0.3° is designated as $P^{7.8}$).

In the present invention, it is preferred that when the intensity of $P^{22.1}$ is taken as 100, the intensity of $P^{7.8}$ is from 0.5 to 30,
the intensity of $P^{8.9}$ is from 0.5 to 30,
the intensity of $P^{27.1}$ is from 3 to 90,
the intensity of $P^{28.1}$ is from 10 to 300,
the intensity of $P^{35.2}$ is from 0.5 to 30,
the intensity of $P^{36.1}$ is from 5 to 50, and
the intensity of $P^{45.2}$ is from 3 to 30.

The intensity of a peak appearing in an XRD pattern can be obtained as follows. For example, a method for obtaining the intensities of $P^{27.1}$ and $P^{28.1}$ is explained below referring to FIG. 2, which is an enlarged view of the XRD pattern of FIG. 1 (XRD pattern of the oxide catalyst obtained in Example 1), showing the range of from about 25° to about 30° in terms of the diffraction angle (2θ).

Figure 2:
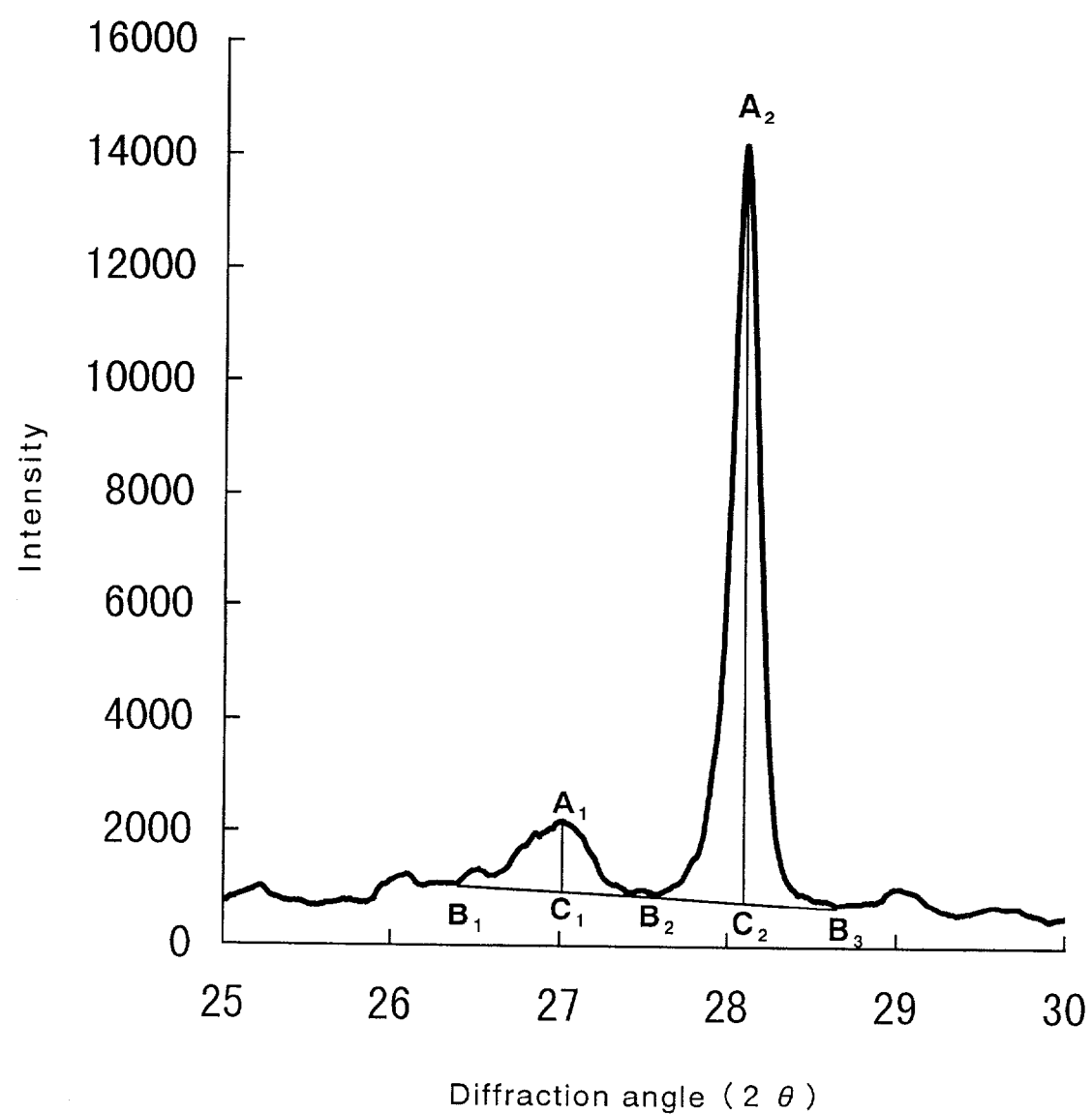
FIG. 2 is an enlarged view of the X-ray diffraction pattern of FIG. 1, showing the range of from 25 to 30° in terms of the diffraction angle (2θ), in order to explain how to obtain the peak intensity ratio.

In FIG. 2, characters $A_1$ and $A_2$ designate the apexes of $P^{27.1}$ and $P^{28.1}$, respectively.

Characters $B_1$, $B_2$ and $B_3$ respectively designate points at which the curved line of the XRD pattern exhibits minimum intensity values in the diffraction angle (2θ) ranges of 26.4±0.3°, 27.6±0.3° and 28.8±0.3°, respectively (these diffraction angle (2θ) ranges are selected to obtain an appropriate base line (i.e., line connecting $B_1$, $B_2$ and $B_3$) for obtaining the intensities of the peaks). In the present invention, usually, each of "the points at which the curved line of the XRD pattern exhibits minimum intensity values" corresponds to a point at which the gradient of a tangential line of the curved line shifts from negative to positive, or a point at which the gradient converges to zero, wherein the gradient is taken in the coordinates of the 2θ-axis and the intensity axis.

Character $C_1$ designates a point at which a line drawn downwardly from peak apex $A_1$ vertically to the 2θ-axis intersects with a straight line connecting points $B_1$ and $B_2$.

Character $C_2$ designates a point at which a line drawn downwardly from peak apex $A_2$ vertically to the 2θ-axis intersects with a straight line connecting points $B_2$ and $B_3$.

The intensity of $P^{27.1}$ is defined as the length of straight line segment $A_1C_1$ which extends from peak apex $A_1$ (of $P^{27.1}$) to point $C_1$; and the intensity of $P^{28.1}$ is defined as the length of straight line segment $A_2C_2$ which extends from peak apex $A_2$ (of $P^{28.1}$) to point $C_2$.

The intensities of other peaks appearing in the XRD pattern can be obtained in substantially the same manner as mentioned above. Specifically, the intensities of other peaks can be obtained as follows.

The intensity of $P^{7.8}$ is defined as the length of straight line segment $A^{7.8}C^{7.8}$ which extends from peak apex $A^{7.8}$ (of $P^{7.8}$) to point $C^{7.8}$, wherein the point $C^{7.8}$ is a point at which a line drawn downwardly from peak apex $A^{7.8}$ vertically to the 2θ-axis intersects with a straight line connecting points $B^{7.1}$ and $B^{9.1}$, wherein points $B^{7.1}$ and $B^{9.1}$ are points at which the curved line of the X-ray diffraction pattern exhibits minimum intensity values in the diffraction angle (2θ) ranges of 7.1±0.3° and 9.1±0.3°, respectively.

The intensity of $P^{8.9}$ is defined as the length of straight line segment $A^{8.9}C^{8.9}$ which extends from peak apex $A^{8.9}$ (of $P^{8.9}$) to point $C^{8.9}$, wherein the point $C^{8.9}$ is a point at which a line drawn downwardly from peak apex $A^{8.9}$ vertically to the 2θ-axis intersects with a straight line connecting points $B^{7.1}$ and $B^{9.1}$, wherein points $B^{7.1}$ and $B^{9.1}$ are points at which the curved line of the X-ray diffraction pattern exhibits its minimum intensity values in the diffraction angle (2θ) ranges of 7.1±0.3° and 9.1±0.3°, respectively.

The intensity of $P^{22.1}$ is defined as the length of straight line segment $A_{22.1}C^{22.1}$ which extends from peak apex $A^{22.1}$ (of $P^{22.1}$) to point $C^{22.1}$, wherein the point $C^{22.1}$ is a point at which a line drawn downwardly from peak apex $A^{22.1}$ vertically to the 2θ-axis intersects with a straight line connecting points $B^{21.1}$ and $B^{22.9}$, wherein points $B^{21.1}$ and $B^{22.9}$ are points at which the curved line of the X-ray diffraction pattern exhibits minimum intensity values in the diffraction angle (2θ) ranges of 21.1±0.3° and 22.9±0.3°, respectively.

The intensity of $P^{35.2}$ is defined as the length of straight line segment $A^{35.2}C^{35.2}$ which extends from peak apex $A^{35.2}$ (of $P^{35.2}$) to point $C^{35.2}$, wherein the point $C^{35.2}$ is a point at which a line drawn downwardly from peak apex $A^{35.2}$ vertically to the 2θ-axis intersects with a straight line connecting points $B^{34.5}$ and $B^{35.7}$, wherein points $B^{34.5}$ and $B^{35.7}$ are points at which the curved line of the X-ray diffraction pattern exhibits minimum intensity values in the diffraction angle (2θ) ranges of 34.5±0.3° and 35.7±0.3°, respectively.

The intensity of $P^{36.1}$ is defined as the length of straight line segment $A^{36.1}C^{36.1}$ which extends from peak apex $A^{36.1}$ (of $P^{36.1}$) to point $C^{36.1}$, wherein the point $C^{36.1}$ is a point at which a line drawn downwardly from peak apex $A^{36.1}$ vertically to the 2θ-axis intersects with a straight line connecting points $B^{35.7}$ and $B^{36.5}$, wherein points $B^{35.7}$ and $B^{36.5}$ are points at which the curved line of the X-ray diffraction pattern exhibits minimum intensity values in the diffraction angle (2θ) ranges of 35.7±0.3° and 36.5±0.3°, respectively.

The intensity of $P^{45.2}$ is defined as the length of straight line segment $A^{45.2}C^{45.2}$ which extends from peak apex $A^{45.2}$ (of $P^{45.2}$) to point $C^{45.2}$, wherein the point $C^{45.2}$ is a point at which a line drawn downwardly from peak apex $A^{45.2}$ vertically to the 2θ-axis intersects with a straight line connecting points $B^{44.5}$ and $B^{45.8}$, wherein points $B^{44.5}$ and $B^{45.8}$ are points at which the curved line of the X-ray diffraction pattern exhibits minimum intensity values in the diffraction angle (2θ) ranges of 44.5±0.3° and 45.8±0.3°, respectively.

In the present invention, it is preferred that the intensity ratio R is from 0.01 to 0.80, advantageously from 0.03 to 0.50, more advantageously from 0.05 to 0.20, wherein R is defined by the following formula:

$$R = I^{27.1}/(I^{27.1} + I^{28.1})$$

wherein:
$I^{27.1}$ represents the intensity of $P^{27.1}$ (the peak appearing at diffraction angle (2θ) of 27.1±0.3°), and
$I^{28.1}$ represents the intensity of $P^{28.1}$ (the peak appearing at diffraction angle (2θ) of 28.1±0.3°).

It is preferred that the oxide catalyst of the present invention further comprises a silica carrier having supported thereon said oxide catalyst. That is, it is preferred that the oxide catalyst of the present invention is a silica-supported catalyst. In the present invention, it is preferred that the silica carrier is present in an amount of from 20 to 60% by weight, more advantageously from 25 to 55% by weight, most advantageously from 40 to 50% by weight, based on the total weight of the oxide catalyst and the silica carrier The weight percentage of silica carrier is defined by the following formula:

weight percentage of silica carrier=($W2/(W1+W2)$)×100 wherein W1 represents the weight of oxide catalyst, which is calculated from the composition of the raw materials and the oxidation numbers of the component elements contained in the raw materials, and W2 represents the weight of silica carrier, in terms of $SiO_2$.

When the amount of silica carrier is less than 20% by weight, disadvantages are likely to occur wherein the strength of the oxide catalyst becomes low, and the selectivity for and yield of (meth)acrylonitrile or (meth)acrylic acid, which are achieved by the use of the oxide catalyst, become low. On the other hand, when the amount of silica carrier is more than 60% by weight, the strength of the oxide catalyst becomes high; however, the selectivity for and yield of (meth)acrylonitrile or (meth)acrylic acid, which are achieved by the use of the oxide catalyst, become low.

Next, an explanation is made below with respect to the compounds used in the process for producing the oxide catalyst of the present invention as sources of the component elements of the oxide catalyst, i.e., compounds used as sources of molybdenum, vanadium, antimony, niobium, and the optional component element Z.

Examples of sources of molybdenum include ammonium heptamolybdate, molybdenum oxides, molybdic acid, molybdenum oxychlorides, molybdenum chlorides, molybdenum alkoxides and the like. Of these, ammonium heptamolybdate is preferred.

Examples of sources of vanadium include ammonium metavanadate, vanadium (V) oxide, vanadium oxychlorides, and vanadium alkoxides. Of these, ammonium metavanadate and vanadium (V) oxide are preferred.

Examples of sources of antimony include antimony(III) oxide, antimony(IV) oxide, antimony(V) oxide, metantimonic acids (III), antimonic acids (V), ammonium antimonate(V), antimony(III) chloride, antimony(III) oxychloride, antimony(III) nitrate oxide, antimony alkoxides, organic acid salts of antimony, such as antimony tartrate, and metallic antimony. Of these, antimony(III) oxide is preferred.

Examples of sources of niobium include niobic acid, niobium oxide, niobium chloride, niobium alkoxides (such as $Nb(OCH_2CH_3)_5$) and organic salts of niobium. Of these, niobic acid is preferred.

Examples of sources of Z elements include oxalic acid salts, hydroxides, oxides, nitrates, acetates, ammonium salts, carbonates and alkoxides of the Z elements.

The suitable amounts of the above-mentioned compounds as sources of the component elements vary depending on the types of the compounds used, and the amounts are appropriately selected such that an oxide catalyst having the composition represented by formula (I) is obtained.

When it is intended to use silica to obtain an oxide catalyst supported on a silica carrier, silica sol can be advantageously used as a source of silica. It is especially preferred to use a silica sol stabilized with ammonium ions.

With respect to the process for producing the oxide catalyst of the present invention, there is no particular limitation. However, it is preferred to produce the oxide catalyst of the present invention by a process comprising the following three steps: a step for providing an aqueous raw material mixture containing compounds of molybdenum, vanadium, antimony, niobium, and optionally component element Z (i.e., step for preparing the aqueous raw material mixture), a step for drying the aqueous raw material mixture, and a step for calcining the resultant dried aqueous raw material mixture.

In the aqueous raw material mixture, the abovementioned compounds used as sources of molybdenum, vanadium, antimony, niobium and the optional component element Z may remain as they are, or may be present in modified forms thereof which are formed by chemical reactions (e.g., chemical reactions between the compounds used as raw materials).

Hereinbelow, explanations are made with respect to the step for providing an aqueous raw material mixture (i.e., step for preparing the aqueous raw material mixture), the step for drying the aqueous raw material mixture, and the step for calcining the resultant dried aqueous raw material mixture, wherein specific modes of the above-mentioned process for producing the oxide catalyst of the present invention are taken as examples.

<Aqueous Raw Material Mixture Preparation Step>

An aqueous mixture containing ammonium heptamolybdate, ammonium metavanadate and antimony(III) oxide is subjected to a reaction, preferably, at 70 to 100° C., while stirring for 1 to 5 hours. The resultant mixture containing molybdenum, vanadium and antimony is subjected to an oxidation by air or an oxidation in a liquid phase by using hydrogen peroxide or the like, to thereby obtain an aqueous mixture (A). It is preferred that the oxidation is conducted to an extent wherein the change in color of the aqueous mixture from dark blue to orange or brown is visually observed. In the case where the oxidation is conducted in a liquid phase by using hydrogen peroxide, the molar ratio of hydrogen peroxide to antimony is preferably 0.5 to 2. The molybdenum concentration of the aqueous mixture (A) is preferably 0.2 mol/kg or more, more preferably 0.5 mol/kg or more.

Alternatively, to an aqueous solution having ammonium heptamolybdate dissolved therein are added antimony(III) oxide and aqueous hydrogen peroxide having a hydrogen peroxide concentration of 0.01 to 30% by weight (preferably 0.1 to 10% by weight), followed by stirring at 50 to 80° C. The molar ratio of hydrogen peroxide to antimony is preferably 0.5 to 5. To the resultant aqueous solution is added ammonium metavanadate to obtain an aqueous mixture (A'). The molybdenum concentration of the aqueous mixture (A') is preferably 0.2 mol/kg or more, more preferably 0.5 mol/kg or more.

On the other hand, a niobium-containing aqueous mixture (B) is prepared by dissolving a niobic acid in an aqueous oxalic acid solution. The niobium concentration of the niobium-containing aqueous mixture (B) is preferably 0.05 mol/kg or more, more preferably 0.15 mol/kg or more. The oxalic acid/niobium molar ratio in the niobium-containing aqueous mixture (B) is preferably in the range of from 1 to 10, more preferably from 2 to 6, most preferably from 2 to 4. For obtaining the above-mentioned preferred oxide catalyst which exhibits, in the X-ray diffraction pattern, peaks at specific diffraction angles, it is especially preferred that the oxalic acid/niobium molar ratio is in the range of from 2 to 4. However, when, prior to the below-described calcination step, pre-calcination is performed, the above-mentioned preferred oxide catalyst can be obtained even if the oxalic acid/niobium molar ratio is not in the range of from 2 to 4, but the molar ratio is preferably in the range of from 1 to 10.

To the obtained niobium-containing aqueous mixture (B) may be added aqueous hydrogen peroxide. The addition of aqueous hydrogen peroxide enables the improvement of performance of the oxide catalyst, that is, it becomes possible to improve the space time yield and the selectivity for the desired compound in a catalytic oxidation or ammoxidation of propane or isobutane in the gaseous phase. When aqueous hydrogen peroxide is added to the niobium-containing aqueous mixture (B), the molar ratio of hydrogen peroxide to niobic acid (in terms of niobium atoms) is preferably in the range of from 0.5 to 10, more preferably from 2 to 6.

By mixing the thus obtained aqueous mixture (A) or (A') with the thus obtained niobium-containing aqueous mixture (B), the aqueous raw material mixture can be obtained. The obtained aqueous raw material mixture is subjected to the below-described drying step.

When it is intended to produce an oxide catalyst supported on a silica carrier, a silica sol may be added at any time during the above-descried procedures to thereby obtain a silica sol-containing aqueous raw material mixture, and the obtained silica sol-containing aqueous raw material mixture is subjected to the below-described drying step.

When it is intended to produce an oxide catalyst containing the Z element which is an optional component, a compound containing the Z element may be added at any time during the above-descried procedures to thereby obtain a Z element-containing aqueous raw material mixture, and the obtained Z element-containing aqueous raw material mixture is subjected to the below-described drying step.

<Drying Step>

The above-obtained aqueous raw material mixture is dried by spray drying or evaporation drying to thereby obtain a dried powder. The spray drying can be conducted by centrifugation, by two-phase flow nozzle method or by high pressure nozzle method. As a heat source for drying, it is preferred to use air which has been heated by steam, an electric heater and the like. It is preferred that the temperature of the heated air at an entrance to the dryer section thereof is from 150 to 300° C. The spray drying can be also conveniently conducted by spraying the aqueous raw material mixture onto an iron plate which has been heated to a temperature of 100 to 300° C.

For obtaining the above-mentioned preferred oxide catalyst which exhibits, in the X-ray diffraction pattern, peaks at specific diffraction angles, it is especially preferred to conduct the drying step by spray drying.

<Calcination Step>

In the calcination step, the dried powder obtained in the drying step is calcined so as to obtain the oxide catalyst of the present invention. The calcination can be conducted by using a kiln, such as a rotary kiln, a tunnel kiln, a muffle kiln or a fluidized-bed kiln. The calcination is conducted in an atmosphere of an inert gas, such as nitrogen gas which is substantially free of oxygen, or alternatively, in an atmosphere containing an oxidative gas (such as an oxygen-containing gas) in combination with a reductive gas (such as a gaseous organic compound (e.g., propane or isobutane) or gaseous ammonia). The calcination is preferably conducted in an atmosphere of an inert gas, such as nitrogen gas which is substantially free of oxygen, more preferably under a flow of an inert gas, at a temperature of 500 to 700° C., preferably 570 to 670° C. The time of calcination is generally 0.5 to 10 hours, preferably 1 to 3 hours. It is preferred that the oxygen concentration of the above-mentioned inert gas is 1000 ppm or less, more advantageously 100 ppm or less, most advantageously 10 ppm or less, as measured by gas chromatography or by means of a trace oxygen analyzer. The calcination can be conducted repeatedly. Prior to the calcination, the dried powder may be subjected to pre-calcination in an atmosphere of air or under a stream of air at 200 to 420° C., preferably 250 to 350° C. for 10 minutes to 5 hours. The catalyst obtained by calcination may be subjected to further calcination in an atmosphere of air at a temperature of from 200 to 400° C. for 5 minutes to 5 hours.

The thus produced oxide catalyst of the present invention can be used as a catalyst for producing (meth)acrylonitrile by ammoxidation of propane or isobutane in the gaseous phase. The oxide catalyst of the present invention can also be used as a catalyst for producing (meth)acrylic acid by oxidation of propane or isobutane in the gaseous phase. The oxide catalyst of the present invention is preferably used as a catalyst for producing (meth)acrylonitrile, more preferably as a catalyst for producing acrylonitrile.

Propane or isobutane used for producing (meth)acrylic acid, and propane or isobutane and ammonia used for producing (meth)acrylonitrile need not be of very high purity but may be of a commercial grade.

Examples of sources of molecular oxygen fed into the reaction system include air, oxygen-rich air, and pure oxygen. Further, such a source of molecular oxygen may be diluted with steam, helium, argon, carbon dioxide, nitrogen or the like.

In the case of an ammoxidation reaction in the gaseous phase, the molar ratio of ammonia to propane or isobutane for the ammoxidation is generally in the range of from 0.1 to 1.5, preferably from 0.2 to 1.2. When the ammoxidation is performed in a recycling mode, the molar ratio of ammonia to propane or isobutane at the entrance of a reactor used is preferably in the range of from 0.2 to 1.0, more preferably from 0.5 to 0.8.

The molar ratio of molecular oxygen to propane or isobutane used for the ammoxidation is preferably in the range of from 0.2 to 6, more preferably from 0.4 to 4. When the ammoxidation is performed in a recycling mode, it is preferred that the molar ratio of molecular oxygen to propane or isobutane at the entrance of the reactor used is preferably in the range of 0.8 to 2.2, more preferably from 1.5 to 1.9.

In the case of an oxidation reaction in the gaseous phase, the molar ratio of molecular oxygen to propane or isobutane used for the oxidation is generally in the range of from 0.1 to 10, preferably from 0.1 to 5. It is preferred that steam is introduced into the reaction system. The molar ratio of steam to propane or isobutane used for the oxidation is generally in the range of from 0.1 to 70, preferably from 3 to 40.

In each of the ammoxidation reaction in the gaseous phase and the oxidation reaction in the gaseous phase, the reaction pressure is generally in the range of from 0.01 to 1 MPa, preferably from 0.1 to 0.3 MPa, in terms of the absolute pressure.

In the ammoxidation reaction in the gaseous phase, the reaction temperature is generally in the range of from 300 to 600° C., preferably from 380 to 470° C.

In the oxidation reaction in the gaseous phase, the reaction temperature is generally in the range of from 300 to 600° C., preferably from 350 to 440° C.

In each of the ammoxidation reaction in the gaseous phase and the oxidation reaction in the gaseous phase, the time of contact (contact time) between gaseous feedstocks (containing propane or isobutane, molecular oxygen and the like) and the catalyst is generally in the range of from 0.1 to 30 (g·sec/ml), preferably from 0.5 to 10 (g·sec/ml). In the present invention, the contact time is determined according to the following formula:

$$\text{Contact time}(g \cdot \sec/ml) = \frac{W}{F} \times 60 \times \frac{273}{273+T} \times \frac{P+0.101}{0.101}$$

wherein:
W represents the weight (g) of the oxide catalyst contained in the reactor;
F represents the flow rate (ml/min) of the gaseous feed stocks;
T represents the reaction temperature (° C.); and
P represents the reaction pressure (MPa) (gauge pressure).

Each of the ammoxidation reaction in the gaseous phase and the oxidation reaction in the gaseous phase can be conducted in a conventional reactor, such as a fixed bed reactor, a fluidized-bed reactor or a moving bed reactor, preferably in a fluidized-bed reactor. The reaction mode may be either a one pass mode or a recycling mode. Of these two reaction modes, a recycling mode is preferred.

BEST MODE FOR CARRYING OUT THE INVENTION

Hereinbelow, the present invention will be described in more detail with reference to the following Examples and Comparative Examples, which should not be construed as limiting the scope of the present invention.

(1) Conversion of Propane, Selectivity for Acrylonitrile and Selectivity for Acrylic Acid:

In the following Examples and Comparative Examples, the results of the oxidation or ammoxidation were evaluated in terms of the conversion (%) of propane, the selectivity (%) for acrylonitrile and the selectivity (%) for acrylic acid, which are, respectively, defined as follows:

$$\text{Conversion (\%) of propane} = \frac{\text{mole of propane reacted}}{\text{mole of propane fed}} \times 100$$

$$\text{Selectivity (\%) for acrylonitrile} = \frac{\text{mole of acrylonitrile formed}}{\text{mole of propane reacted}} \times 100$$

$$\text{Selectivity (\%) for acrylic acid} = \frac{\text{mole of acrylic acid formed}}{\text{mole of propane reacted}} \times 100$$

(2) X-Ray Diffractometry of Oxide Catalyst:

An X-ray diffraction (XRD) pattern of the oxide catalyst was obtained by subjecting the oxide catalyst to measurement by X-ray diffractometry using an X-ray diffractometer MXP-18 (manufactured and sold by MAC Science Ltd., Japan). The method for preparing a sample and XRD pattern measurement conditions are as follows.

<Preparation of a Sample>

About 0.5 g of the catalyst was placed in an agate mortar and subjected to grinding for 2 minutes by manually operating an agate pestle. The resultant catalyst powder was subjected to sifting, to thereby obtain a powdery catalyst having a particle size of 53 μm or less. The obtained powdery catalyst was placed on a sample-holding table for an XRD pattern measurement. The table had a rectangular recess in the surface thereof (which has the following dimensions: a length of 20 mm, a width of 16 mm and a depth of 0.2 mm), and the powdery catalyst in the recess was pressed using a stainless steel spatula having a flat shape so that the surface of the powdery catalyst became flat.

<XRD Pattern Measurement Conditions>

An XRD pattern measurement was conducted under the following conditions.

| | |
|---|---|
| Source of X-ray | $CuK_{\alpha 1} + CuK_{\alpha 2}$ |
| Detector | Scintillation counter |
| Single crystal used for a monochromator | Graphite |
| Tube voltage | 40 kV |
| Tube current | 190 mA |
| Divergence slit | 1° |
| Scatter slit | 1° |
| Receiving slit | 0.3 mm |
| Scanning speed | 5°/min. |
| Sampling interval | 0.02° |
| Scanning method | 2θ/θ method |

The diffraction angle (2θ) correction was conducted by performing a calibration using X-ray diffractometry data obtained with respect to a silicon powder. Further, a smoothing treatment of the XRD pattern was performed.

With respect to the obtained XRD pattern, the intensity ratio R is defined by the following formula:

$$R = I^{27.1}/(I^{27.1} + I^{28.1})$$

wherein:
$I^{27.1}$ represents the intensity of $P^{27.1}$ (the peak appearing at diffraction angle (2θ) of 27.1±0.3°), and
$I^{28.1}$ represents the intensity of $P^{28.1}$ (the peak appearing at diffraction angle (2θ) 28.1±0.3°).

EXAMPLE 1

(Preparation of a Catalyst)

An oxide catalyst represented by the formula: $Mo_1V_{0.23}Sb_{0.26}Nb_{0.09}O_n/SiO_2$(45% by weight) was prepared as follows.

To 1,000 g of water were added 250 g of ammonium heptamolybdate [$(NH_4)_6Mo_7O_{24} \cdot 4H_2O$], 38.1 g of ammonium metavanadate ($NH_4VO_3$) and 53.6 g of antimony(III) oxide ($Sb_2O_3$), and the resultant mixture was subjected to a reaction under reflux in an oil bath in the air at 100° C. for 2 hours, followed by cooling to 50° C. Subsequently, to the resultant reaction mixture was added 829 g of a silica sol having an $SiO_2$ content of 30% by weight, followed by stirring for 30 minute. Then, to the resultant mixture was further added 250 g of 5 wt % aqueous hydrogen peroxide, and the resultant mixture was stirred at 50° C. for 1 hour to effect an oxidation treatment, to thereby obtain an aqueous mixture (A). By the oxidation treatment, the color of the mixture changed from dark blue to brown.

On the other hand, to 150 g of water were added 22.3 g of niobic acid ($Nb_2O_5$ content: 76% by weight) and 43.4 g of oxalic acid dehydrate ($H_2C_2O_4 \cdot 2H_2O$), and the resultant mixture was heated at 60° C. while stirring to dissolve the niobic acid and oxalic acid dihydrate in the water, followed by cooling to 30° C., to thereby obtain an aqueous niobium-oxalic acid solution (B).

The thus obtained aqueous niobium-oxalic acid solution (B) was added to the above-prepared aqueous mixture (A), and the resultant mixture was stirred at 50° C. for 30 minutes in the air, to thereby obtain an aqueous raw material mixture.

The obtained aqueous raw material mixture was subjected to a spray drying by means of a centrifugation type spray-drying apparatus under conditions wherein the entrance and exit temperatures of the dryer of the spray-drying apparatus were 230° C. and 120° C., respectively, to thereby obtain a dried powder comprised of spherical particles. 100 g of the obtained dried powder was charged into a quartz container and calcined in a kiln at 640° C. for 2 hours under a flow of nitrogen gas at a flow rate of 600 Nml/min. (Nml means ml as measured under the normal temperature and pressure conditions, namely, at 0° C. under 1 atm.) while rotating the quartz container, to thereby obtain an oxide catalyst. The oxygen concentration of the nitrogen gas used for the calcination was determined by means of a trace oxygen analyzer (Model 306WA, manufactured and sold by Teledyne Analytical Instruments, U.S.A.), and it was found that the oxygen concentration of the nitrogen gas was 1 ppm.

The composition of the oxide catalyst and the important conditions in the catalyst production process are shown in Table 1.

With respect to the obtained oxide catalyst, the X-ray diffraction (XRD) pattern obtained using $CuK_\alpha$ as a source of X-ray is shown in FIG. 1.

The obtained oxide catalyst exhibited, in an XRD pattern thereof, peaks at diffraction angles (2θ) of 7.8±0.3°, 8.9±0.3°, 22.1±0.3°, 27.1±0.3°, 28.1±0.3°, 35.2±0.3°, 36.1±0.3° and 45.2±0.3°, wherein R=0.08.

(Ammoxidation of Propane)

0.35 g of the obtained oxide catalyst (W=0.35 g) was charged into a fixed-bed type reaction tube having an inner diameter of 4 mm. A gaseous feedstock mixture having a molar ratio of propane:ammonia:oxygen:helium of 1:0.7:1.7:5.3 was fed into the reaction tube at a flow rate (F) of 3.6 (ml/min). The reaction temperature (T) (external temperature) was 420° C. and the reaction pressure (P) was 0 MPa in terms of the gauge pressure. The contact time between the oxide catalyst and the gaseous mixture of the feedstocks was 2.3 (g·sec/ml). The contact time was obtained by the following formula:

$$\text{Contact time} = \frac{W}{F} \times 60 \times \frac{273}{273+T} \times \frac{P+0.101}{0.101}$$

The produced gaseous reaction mixture was analyzed by means of an on-line gas chromatography apparatus. The results are shown in Table 1.

EXAMPLE 2

(Preparation of a Catalyst)

An oxide catalyst represented by the formula: $Mo_1V_{0.23}Sb_{0.25}Nb_{0.09}O_n/SiO_2$ (45% by weight) was prepared as follows.

Preparation of an oxide catalyst was performed in substantially the same manner as in Example 1, except that the amount of antimony(III) oxide ($Sb_2O_3$) was changed from 53.6 g to 51.6 g, the amount of 5 wt % aqueous hydrogen peroxide was changed from 250 g to 241 g and the amount of silica sol was changed from 829 g to 823 g.

The composition of the oxide catalyst and the important conditions in the catalyst production process are shown in Table 1.

The obtained oxide catalyst exhibited, in an XRD pattern thereof, peaks at diffraction angles (2θ) of 7.8±0.3°, 8.9±0.3°, 22.1±0.3°, 27.1±0.3°, 28.1±0.3°, 35.2±0.3°, 36.1±0.3° and 45.2±0.3°, wherein R=0.09.

(Ammoxidation of Propane)

Using the obtained oxide catalyst, the ammoxidation reaction of propane was performed in the same manner as in Example 1. The results are shown in Table 1.

EXAMPLE 3

(Preparation of a Catalyst)

An oxide catalyst represented by the formula: $Mo_1V_{0.24}Sb_{0.25}Nb_{0.09}O_n/SiO_2$ (45% by weight) was prepared as follows.

Preparation of an oxide catalyst was performed in substantially the same manner as in Example 1, except that the amount of ammonium metavanadate ($NH_4VO_3$) was changed from 38.1 g to 39.7 g, the amount of antimony(III) oxide ($Sb_2O_3$) was changed from 53.6 g to 51.6 g, the amount of 5 wt % aqueous hydrogen peroxide was changed from 250 g to 241 g and the amount of silica sol was changed from 829 g to 827 g.

The composition of the oxide catalyst and the important conditions in the catalyst production process are shown in Table 1.

The obtained oxide catalyst exhibited, in an XRD pattern thereof, peaks at diffraction angles (2θ) of 7.8±0.3°, 8.9±0.3°, 22.1±0.3°, 27.1±0.3°, 28.1±0.3°, 35.2±0.3°, 36.1±0.3° and 45.2±0.3°, wherein R=0.09.

(Ammoxidation of Propane)

Using the obtained oxide catalyst, the ammoxidation reaction of propane was performed in the same manner as in Example 1. The results are shown in Table 1.

EXAMPLE 4

(Preparation of a Catalyst)

An oxide catalyst represented by the formula: $Mo_1V_{0.24}Sb_{0.26}Nb_{0.09}O_n/SiO_2$ (45% by weight) was prepared as follows.

Preparation of an oxide catalyst was performed in substantially the same manner as in Example 1, except that the amount of ammonium metavanadate ($NH_4VO_3$) was changed from 38.1 g to 39.7 and the amount of silica sol was changed from 829 g to 833 g.

The composition of the oxide catalyst and the important conditions in the catalyst production process are shown in Table 1.

The obtained oxide catalyst exhibited, in an XRD pattern thereof, peaks at diffraction angles (2θ) of 7.8±0.3°, 8.9±0.3°, 22.1±0.3°, 27.1±0.3°, 28.1±0.3°, 35.2±0.3°, 36.1±0.3° and 45.2±0.3°, wherein R=0.10.

(Ammoxidation of Propane)

Using the obtained oxide catalyst, the ammoxidation reaction of propane was performed in the same manner as in Example 1. The results are shown in Table 1.

EXAMPLE 5

(Preparation of a Catalyst)

An oxide catalyst represented by the formula: $Mo_1V_{0.25}Sb_{0.26}Nb_{0.09}O_n/SiO_2$ (45% by weight) was prepared as follows.

Preparation of an oxide catalyst was performed in substantially the same manner as in Example 1, except that the amount of ammonium metavanadate ($NH_4VO_3$) was changed from 38.1 g to 41.4 g and the amount of silica sol was changed from 829 g to 836 g.

The composition of the oxide catalyst and the important conditions in the catalyst production process are shown in Table 1.

The obtained oxide catalyst exhibited, in an XRD pattern thereof, peaks at diffraction angles (2θ) of 7.8±0.3°, 8.9±0.3°, 22.1±0.3°, 27.1±0.3°, 28.1±0.3°, 35.2±0.3°, 36.1±0.3° and 45.2±0.3°, wherein R=0.10.

(Ammoxidation of Propane)

Using the obtained oxide catalyst, the ammoxidation reaction of propane was performed in the same manner as in Example 1. The results are shown in Table 1.

EXAMPLE 6

(Preparation of a Catalyst)

An oxide catalyst represented by the formula: $Mo_1V_{0.20}Sb_{0.29}Nb_{0.11}O_n/SiO_2$(45% by weight) was prepared as follows.

Preparation of an oxide catalyst was performed in substantially the same manner as in Example 1, except that:

in the preparation of aqueous mixture (A), the amount of ammonium metavanadate ($NH_4VO_3$) was changed from 38.1 g to 33.1 g, the amount of antimony(III) oxide ($Sb_2O_3$) was changed from 53.6 g to 59.8 g, the amount of 5 wt % aqueous hydrogen peroxide was changed from 250 g to 279 g and the amount of silica sol was changed from 829 g to 846 g; and in the preparation of aqueous niobium-oxalic acid solution (B), the amount of water was changed from 150 g to 180 g, the amount of niobic acid was changed from 22.3 g to 27.2 g and the amount of oxalic acid dihydrate was changed from 43.4 g to 53.0 g.

The composition of the oxide catalyst and the important conditions in the catalyst production process are shown in Table 1.

The obtained oxide catalyst exhibited, in an XRD pattern thereof, peaks at diffraction angles (2θ) of 7.8±0.3°, 8.9±0.3°, 22.1±0.3°, 27.1±0.3°, 28.1±0.3°, 35.2±0.3°, 36.1±0.3° and 45.2±0.3°, wherein R=0.14.

(Ammoxidation of Propane)

Using the obtained oxide catalyst, the ammoxidation reaction of propane was performed in substantially the same manner as in Example 1, except that flow rate (F) of the gaseous feedstock mixture was changed from 3.6 (ml/min) to 3.3 (ml/min) and the contact time was changed from 2.3 (g·sec/ml) to 2.5 (g·sec/ml). The results are shown in Table 1.

EXAMPLE 7

(Preparation of a Catalyst)

An oxide catalyst represented by the formula: $Mo_1V_{0.22}Sb_{0.26}Nb_{0.09}O_n/SiO_2$(45% by weight) was prepared as follows.

Preparation of an oxide catalyst was performed in substantially the same manner as in Example 1, except that the amount of ammonium metavanadate ($NH_4VO_3$) was changed from 38.1 g to 36.4 g and the amount of silica sol was changed from 829 g to 825 g.

The composition of the oxide catalyst and the important conditions in the catalyst production process are shown in Table 1.

The obtained oxide catalyst exhibited, in an XRD pattern thereof, peaks at diffraction angles (2θ) of 7.8±0.3°, 8.9±0.3°, 22.1±0.3°, 27.1±0.3°, 28.1±0.3°, 35.2±0.3°, 36.1±0.3° and 45.2±0.3°, wherein R=0.08.

(Ammoxidation of Propane)

Using the obtained oxide catalyst, the ammoxidation reaction of propane was performed in the same manner as in Example 1. The results are shown in Table 1.

EXAMPLE 8

(Preparation of a catalyst)

An oxide catalyst represented by the formula: $Mo_1V_{0.22}Sb_{0.27}Nb_{0.10}O_n/SiO_2$(45% by weight) was prepared as follows.

Preparation of an oxide catalyst was performed in substantially the same manner as in Example 1, except that:

in the preparation of aqueous mixture (A), the amount of ammonium metavanadate was changed from 38.1 g to 36.4 g, the amount of antimony(III) oxide was changed from 53.6 g to 55.7 g, the amount of 5 wt % aqueous hydrogen peroxide was changed from 250 g to 260 g and the amount of silica sol was changed from 829 g to 836 g; and in the preparation of aqueous niobium-oxalic acid solution (B), the amount of water was changed from 150 g to 165 g, the amount of niobic acid was changed from 22.3 g to 24.7 g and the amount of oxalic acid dihydrate was changed from 43.4 g to 48.2 g.

The composition of the oxide catalyst and the important conditions in the catalyst production process are shown in Table 1.

The obtained oxide catalyst exhibited, in an XRD pattern thereof, peaks at diffraction angles (2θ) of 7.8±0.3°, 8.9±0.3°, 22.1±0.3°, 27.1±0.3°, 28.1±0.3°, 35.2±0.3°, 36.1±0.3° and 45.2±0.3°, wherein R=0.12.

(Ammoxidation of Propane)

Using the obtained oxide catalyst, the ammoxidation reaction of propane was performed in substantially the same manner as in Example 1, except that flow rate (F) of the gaseous feedstock mixture was changed from 3.6 (ml/min) to 3.4 (ml/min) and the contact time was changed from 2.3 (g·sec/ml) to 2.4 (g·sec/ml). The results are shown in Table 1.

EXAMPLE 9

(Preparation of a Catalyst)

An oxide catalyst represented by the formula: $Mo_1V_{0.17}Sb_{0.30}Nb_{0.12}O_n/SiO_2$(45% by weight) was prepared as follows.

Preparation of an oxide catalyst was performed in substantially the same manner as in Example 1, except that:

in the preparation of aqueous mixture (A), the amount of ammonium metavanadate was changed from 38.1 g to 28.2 g, the amount of antimony(III) oxide was changed from 53.6 g to 61.9 g, the amount of 5 wt % aqueous hydrogen peroxide was changed from 250 g to 289 g and the amount of silica sol was changed from 829 g to 846 g; and in the preparation of aqueous niobium-oxalic acid solution (B), the amount of water was changed from 150 g to 200 g, the amount of niobic acid was changed from 22.3 g to 29.7 g and the amount of oxalic acid dihydrate was changed from 43.4 g to 57.8 g.

The composition of the oxide catalyst and the important conditions in the catalyst production process are shown in Table 1.

The obtained oxide catalyst exhibited, in an XRD pattern thereof, peaks at diffraction angles (2θ) of 7.8±0.3°, 8.9±0.3°, 22.1±0.3°, 27.1±0.3°, 28.1±0.3°, 35.2±0.3°, 36.1±0.3° and 45.2±0.3°, wherein R=0.16.

(Ammoxidation of Propane)

Using the obtained oxide catalyst, the ammoxidation reaction of propane was performed in substantially the same manner as in Example 1, except that flow rate (F) of the gaseous feedstock mixture was changed from 3.6 (ml/min) to 3.2 (ml/min) and the contact time was changed from 2.3 (g·sec/ml) to 2.6 (g·sec/ml). The results are shown in Table 1.

EXAMPLE 10

(Preparation of a Catalyst)

An oxide catalyst represented by the formula: $Mo_1V_{0.23}Sb_{0.25}Nb_{0.09}O_n/SiO_2$(40% by weight) was prepared as follows.

Preparation of an oxide catalyst was performed in substantially the same manner as in Example 1, except that the amount of antimony(III) oxide ($Sb_2O_3$) was changed from 53.6 g to 51.6 g, the amount of 5 wt % aqueous hydrogen peroxide was changed from 250 g to 241 g and the amount of silica sol was changed from 829 g to 671 g.

The composition of the oxide catalyst and the important conditions in the catalyst production process are shown in Table 1.

The obtained oxide catalyst exhibited, in an XRD pattern thereof, peaks at diffraction angles (2θ) of 7.8±0.3°, 8.9±0.3°, 22.1±0.3°, 27.1±0.3°, 28.1±0.3°, 35.2±0.3°, 36.1±0.3° and 45.2±0.3°, wherein R=0.10.

(Ammoxidation of Propane)

Using the obtained oxide catalyst, the ammoxidation reaction of propane was performed in substantially the same manner as in Example 1, except that flow rate (F) of the gaseous feedstock mixture was changed from 3.6 (ml/min) to 4.0 (ml/min) and the contact time was changed from 2.3 (g·sec/ml) to 2.1 (g·sec/ml). The results are shown in Table 1.

EXAMPLE 11

(Preparation of a Catalyst)

An oxide catalyst represented by the formula: $Mo_1V_{0.23}Sb_{0.26}Nb_{0.09}O_n/SiO_2$(45% by weight) was prepared as follows.

Preparation of an oxide catalyst was performed in substantially the same manner as in Example 1, except that 173 g of 5 wt % aqueous hydrogen peroxide was further added to aqueous niobium-oxalic acid solution (B).

The composition of the oxide catalyst and the important conditions in the catalyst production process are shown in Table 1.

The obtained oxide catalyst exhibited, in an XRD pattern thereof, peaks at diffraction angles (2θ) of 7.8±0.3°, 8.9±0.3°, 22.1±0.3°, 27.1±0.3°, 28.1±0.3°, 35.2±0.3°, 36.1±0.3° and 45.2±0.3°, wherein R=0.08.

(Ammoxidation of Propane)

Using the obtained oxide catalyst, the ammoxidation reaction of propane was performed in substantially the same manner as in Example 1, except that flow rate (F) of the gaseous feedstock mixture was changed from 3.6 (ml/min) to 4.7 (ml/min) and the contact time was changed from 2.3 (g·sec/ml) to 1.7 (g·sec/ml). The results are shown in Table 1.

COMPARATIVE EXAMPLE 1

(Preparation of a catalyst)

An oxide catalyst represented by the formula: $Mo_1V_{0.30}Sb_{0.23}Nb_{0.07}O_n/SiO_2$(45% by weight) was prepared as follows.

Preparation of an oxide catalyst was performed in substantially the same manner as in Example 1, except that:

in the preparation of aqueous mixture (A), the amount of ammonium metavanadate was changed from 38.1 g to 49.7 g, the amount of antimony(III) oxide was changed from 53.6 g to 47.5 g, the amount of 5 wt % aqueous hydrogen peroxide was changed from 250 g to 221 g and the amount of silica sol was changed from 829 g to 826 g; and in the preparation of aqueous niobium-oxalic acid solution (B), the amount of water was changed from 150 g to 116 g, the amount of niobic acid was changed from 22.3 g to 17.3 g and the amount of oxalic acid dihydrate was changed from 43.4 g to 33.7 g.

The composition of the oxide catalyst and the important conditions in the catalyst production process are shown in Table 2.

The obtained oxide catalyst exhibited, in an XRD pattern thereof, peaks at diffraction angles (2θ) of 7.8±0.3°, 8.9±0.3°, 22.1±0.3°, 27.1±0.3°, 28.1±0.3°, 35.2±0.3°, 36.1±0.3° and 45.2±0.3°, wherein R=0.18.

(Ammoxidation of Propane)

Using the obtained oxide catalyst, the ammoxidation reaction of propane was performed in substantially the same manner as in Example 1. The results are shown in Table 2.

COMPARATIVE EXAMPLE 2

(Preparation of a Catalyst)

An oxide catalyst represented by the formula: $Mo_1V_{0.30}Sb_{0.15}Nb_{0.05}O_n/SiO_2$(45% by weight) was prepared as follows.

Preparation of an oxide catalyst was performed in substantially the same manner as in Example 1, except that:

in the preparation of aqueous mixture (A), the amount of ammonium metavanadate was changed from 38.1 g to 49.7 g, the amount of antimony(III) oxide was changed from 53.6 g to 30.9 g, the amount of 5 wt % aqueous hydrogen peroxide was changed from 250 g to 144 g and the amount of silica sol was changed from 829 g to 771 g; and in the preparation of aqueous niobium-oxalic acid solution (B), the amount of water was changed from 150 g to 83 g, the amount of niobic acid was changed from 22.3 g to 12.4 g and the amount of oxalic acid dihydrate was changed from 43.4 g to 24.1 g.

The composition of the oxide catalyst and the important conditions in the catalyst production process are shown in Table 2.

The obtained oxide catalyst exhibited, in an XRD pattern thereof, peaks at diffraction angles (2θ) of 7.8±0.3°, 8.9±0.3°, 22.1±0.3°, 27.1±0.3°, 28.1±0.3°, 35.2±0.3°, 36.1±0.3° and 45.2±0.3°, wherein R=0.10.

(Ammoxidation of Propane)

Using the obtained oxide catalyst, the ammoxidation reaction of propane was performed in substantially the same manner as in Example 1, except that flow rate (F) of the gaseous feedstock mixture was changed from 3.6 (ml/min) to 3.7 (ml/min) and the contact time was changed from 2.3 (g·sec/ml) to 2.2 (g·sec/ml). The results are shown in Table 2.

COMPARATIVE EXAMPLE 3

(Preparation of a Catalyst)

An oxide catalyst represented by the formula: $Mo_1V_{0.30}Sb_{0.20}Nb_{0.05}O_n/SiO_2$(45% by weight) was prepared as follows.

Preparation of an oxide catalyst was performed in substantially the same manner as in Example 1, except that:

in the preparation of aqueous mixture (A), the amount of ammonium metavanadate was changed from 38.1 g to 49.7 g, the amount of antimony(III) oxide was changed from 53.6 g to 41.3 g, the amount of 5 wt % aqueous hydrogen peroxide was changed from 250 g to 192 g and the amount of silica sol was changed from 829 g to 800 g; and in the preparation of aqueous niobium-oxalic acid solution (B), the amount of water was changed from 150 g to 83 g, the amount of niobic acid was changed from 22.3 g to 12.4 g and the amount of oxalic acid dihydrate was changed from 43.4 g to 24.1 g.

The composition of the oxide catalyst and the important conditions in the catalyst production process are shown in Table 2.

The obtained oxide catalyst exhibited, in an XRD pattern thereof, peaks at diffraction angles (2θ) of 7.8±0.3°, 8.9±0.3°, 22.1±0.3°, 27.1±0.3°, 28.1±0.3°, 35.2±0.3°, 36.1±0.3° and 45.2±0.3°, wherein R=0.12.

(Ammoxidation of Propane)

Using the obtained oxide catalyst, the ammoxidation reaction of propane was performed in substantially the same manner as in Example 1. The results are shown in Table 2.

COMPARATIVE EXAMPLE 4

(Preparation of a Catalyst)

An oxide catalyst represented by the formula: $Mo_1V_{0.25}Sb_{0.5}Nb_{0.125}O_n/SiO_2$(45% by weight) was prepared as follows.

Preparation of an oxide catalyst was performed in substantially the same manner as in Example 1, except that:

in the preparation of aqueous mixture (A), the amount of ammonium metavanadate was changed from 38.1 g to 41.4 g, the amount of antimony(III) oxide was changed from 53.6 g to 103.2 g, the amount of 5 wt % aqueous hydrogen peroxide was changed from 250 g to 481 g and the amount of silica sol was changed from 829 g to 989 g; and in the preparation of aqueous niobium-oxalic acid solution (B), the amount of water was changed from 150 g to 210 g, the amount of niobic acid was changed from 22.3 g to 30.9 g and the amount of oxalic acid dihydrate was changed from 43.4 g to 60.3 g.

The composition of the oxide catalyst and the important conditions in the catalyst production process are shown in Table 2.

The obtained oxide catalyst exhibited, in an XRD pattern thereof, peaks at diffraction angles (2θ) of 22.1±0.3°, 28.1±0.3°, 36.1±0.3° and 45.2±0.3°, but not at diffraction angles (2θ) of 7.8±0.3°, 8.9±0.3°, 27.1±0.3° and 35.2±0.3°.

(Ammoxidation of Propane)

Using the obtained oxide catalyst, the ammoxidation reaction of propane was performed in substantially the same manner as in Example 1, except that flow rate (F) of the gaseous feedstock mixture was changed from 3.6 (ml/min) to 2.0 (ml/min) and the contact time was changed from 2.3 (g·sec/ml) to 4.2 (g·sec/ml). The results are shown in Table 2.

COMPARATIVE EXAMPLE 5

(Preparation of a Catalyst)

An oxide catalyst represented by the formula: $Mo_1V_{0.3}Sb_{0.3}Nb_{0.1}O_n/SiO_2$(45% by weight) was prepared as follows.

Preparation of an oxide catalyst was performed in substantially the same manner as in Example 1, except that:

in the preparation of aqueous mixture (A), the amount of ammonium metavanadate was changed from 38.1 g to 49.7 g, the amount of antimony(III) oxide was changed from 53.6 g to 61.9 g, the amount of 5 wt % aqueous hydrogen peroxide was changed from 250 g to 289 g and the amount of silica sol was changed from 829 g to 881 g; and in the preparation of aqueous niobium-oxalic acid solution (B), the amount of water was changed from 150 g to 166 g, the amount of niobic acid was changed from 22.3 g to 24.7 g and the amount of oxalic acid dihydrate was changed from 43.4 g to 48.2 g.

The composition of the oxide catalyst and the important conditions in the catalyst production process are shown in Table 2.

The obtained oxide catalyst exhibited, in an XRD pattern thereof, peaks at diffraction angles (2θ) of 7.8±0.3°, 8.9±0.3°, 22.1±0.3°, 27.1±0.3°, 28.1±0.3°, 35.2±0.3°, 36.1±0.3° and 45.2±0.3°, wherein R=0.06.

(Ammoxidation of Propane)

Using the obtained oxide catalyst, the ammoxidation reaction of propane was performed in substantially the same manner as in Example 1. The results are shown in Table 2.

COMPARATIVE EXAMPLE 6

(Preparation of a Catalyst)

An oxide catalyst represented by the formula: $Mo_1V_{0.3}Sb_{0.3}Nb_{0.05}O_n/SiO_2$(45% by weight) was prepared as follows.

Preparation of an oxide catalyst was performed in substantially the same manner as in Example 1, except that:

in the preparation of aqueous mixture (A), the amount of ammonium metavanadate was changed from 38.1 g to 49.7 g, the amount of antimony(III) oxide was changed from 53.6 g to 61.9 g, the amount of 5 wt % aqueous hydrogen peroxide was changed from 250 g to 289 g and the amount of silica sol was changed from 829 g to 855 g; and in the preparation of aqueous niobium-oxalic acid solution (B), the amount of water was changed from 150 g to 84 g, the amount of niobic acid was changed from 22.3 g to 12.4 g and the amount of oxalic acid dihydrate was changed from 43.4 g to 24.1 g.

The composition of the oxide catalyst and the important conditions in the catalyst production process are shown in Table 2.

The obtained oxide catalyst exhibited, in an XRD pattern thereof, peaks at diffraction angles (2θ) of 7.8±0.3°, 8.9±0.3°, 22.1±0.3°, 27.1±0.3°, 28.1±0.3°, 35.2±0.3°, 36.1±0.3° and 45.2±0.3°, wherein R=0.12.

(Ammoxidation of Propane)

Using the obtained oxide catalyst, the ammoxidation reaction of propane was performed in substantially the same manner as in Example 1, except that flow rate (F) of the gaseous feedstock mixture was changed from 3.6 (ml/min) to 2.0 (ml/min) and the contact time was changed from 2.3 (g·sec/ml) to 4.2 (g·sec/ml). The results are shown in Table 2.

COMPARATIVE EXAMPLE 7

(Preparation of a Catalyst)

An oxide catalyst represented by the formula: $Mo_1V_{0.3}Sb_{0.3}O_n/SiO_2$(45% by weight) was prepared as follows.

Preparation of an oxide catalyst was performed in substantially the same manner as in Example 1, except that:

in the preparation of aqueous mixture (A), the amount of ammonium metavanadate was changed from 38.1 g to 49.7 g, the amount of antimony(III) oxide was changed from 53.6 g to 61.9 g, the amount of 5 wt % aqueous hydrogen peroxide was changed from 250 g to 289 g and the amount of silica sol was changed from 829 g to 830 g; and aqueous niobium-oxalic acid solution (B) was not used.

The composition of the oxide catalyst and the important conditions in the catalyst production process are shown in Table 2.

The obtained oxide catalyst exhibited, in an XRD pattern thereof, peaks at diffraction angles (2θ) of 22.1±0.3°, 27.1±0.3°, 28.1±0.3°, 35.2±0.3°, 36.1±0.3° and 45.2±0.3°, but not at diffraction angles (2θ) of 7.8±0.3° and 8.9±0.3°.

(Ammoxidation of Propane)

Using the obtained oxide catalyst, the ammoxidation reaction of propane was performed in substantially the same manner as in Example 1, except that flow rate (F) of the gaseous feedstock mixture was changed from 3.6 (ml/min) to 2.0 (ml/min) and the contact time was changed from 2.3 (g·sec/ml) to 4.2 (g·sec/ml). The results are shown in Table 2.

TABLE 1

| | | Conditions of the catalyst production process[*1] | | | Contact time (S) | Ammoxidation of propane[*2] | |
|---|---|---|---|---|---|---|---|
| | Composition | $H_2C_2O_4$/ Nb | $H_2O_2$/ Sb | $H_2O_2$/ Nb | | Conversion of propane (%) | Selectivity for acrylonitrile (%) |
| Ex. 1 | $Mo_1V_{0.23}Sb_{0.26}Nb_{0.09}O_n/SiO_2$(45 wt %) | 2.7 | 1 | 0 | 2.3 | 48.5 | 66.4 |
| Ex. 2 | $Mo_1V_{0.23}Sb_{0.25}Nb_{0.09}O_n/SiO_2$(45 wt %) | 2.7 | 1 | 0 | 2.3 | 48.4 | 66.4 |
| Ex. 3 | $Mo_1V_{0.24}Sb_{0.25}Nb_{0.09}O_n/SiO_2$(45 wt %) | 2.7 | 1 | 0 | 2.3 | 48.6 | 66.1 |
| Ex. 4 | $Mo_1V_{0.24}Sb_{0.26}Nb_{0.09}O_n/SiO_2$(45 wt %) | 2.7 | 1 | 0 | 2.3 | 48.2 | 66.2 |
| Ex. 5 | $Mo_1V_{0.25}Sb_{0.26}Nb_{0.09}O_n/SiO_2$(45 wt %) | 2.7 | 1 | 0 | 2.3 | 48.1 | 66.0 |
| Ex. 6 | $Mo_1V_{0.20}Sb_{0.29}Nb_{0.11}O_n/SiO_2$(45 Wt %) | 2.7 | 1 | 0 | 2.5 | 48.9 | 64.8 |
| Ex. 7 | $Mo_1V_{0.22}Sb_{0.26}Nb_{0.09}O_n/SiO_2$(45 wt %) | 2.7 | 1 | 0 | 2.3 | 48.7 | 65.8 |
| Ex. 8 | $Mo_1V_{0.22}Sb_{0.27}Nb_{0.10}O_n/SiO_2$(45 wt %) | 2.7 | 1 | 0 | 2.4 | 48.7 | 65.5 |
| Ex. 9 | $Mo_1V_{0.17}Sb_{0.30}Nb_{0.12}O_n/SiO_2$(45 wt %) | 2.7 | 1 | 0 | 2.6 | 48.2 | 64.8 |
| Ex. 10 | $Mo_1V_{0.23}Sb_{0.25}Nb_{0.09}O_n/SiO_2$(40 wt %) | 2.7 | 1 | 0 | 2.1 | 49.0 | 66.8 |
| Ex. 11 | $Mo_1V_{0.23}Sb_{0.26}Nb_{0.09}O_n/SiO_2$(45 Wt %) | 2.7 | 1 | 2 | 1.7 | 49.5 | 68.0 |

TABLE 2

| | | Conditions of the catalyst production process[*1] | | | Contact time (S) | Ammoxidation of propane[*2] | |
|---|---|---|---|---|---|---|---|
| | Composition | $H_2C_2O_4$/ Nb | $H_2O_2$/ Sb | $H_2O_2$/ Nb | | Conversion of propane (%) | Selectivity for acrylonitrile (%) |
| Com. Ex. 1 | $Mo_1V_{0.30}Sb_{0.23}Nb_{0.07}O_n/SiO_2$ (45 wt %) | 2.7 | 1 | 0 | 2.3 | 48.3 | 63.3 |
| Com. Ex. 2 | $Mo_1V_{0.30}Sb_{0.15}Nb_{0.05}O_n/SiO_2$ (45 wt %) | 2.7 | 1 | 0 | 2.2 | 48.8 | 61.3 |
| Com. Ex. 3 | $Mo_1V_{0.30}Sb_{0.20}Nb_{0.05}O_n/SiO_2$ (45 wt %) | 2.7 | 1 | 0 | 2.3 | 48.6 | 62.8 |
| Com. Ex. 4 | $Mo_1V_{0.25}Sb_{0.5}Nb_{0.125}O_n/SiO_2$ (45 wt %) | 2.7 | 1 | 0 | 4.2 | 9.0 | 23.0 |
| Com. Ex. 5 | $Mo_1V_{0.3}Sb_{0.3}Nb_{0.1}O_n/SiO_2$ (45 wt %) | 2.7 | 1 | 0 | 2.3 | 40.0 | 53.0 |
| Com. Ex. 6 | $Mo_1V_{0.3}Sb_{0.3}Nb_{0.05}O_n/SiO_2$ (45 wt %) | 2.7 | 1 | 0 | 4.2 | 34.0 | 49.1 |
| Com. Ex. 7 | $Mo_1V_{0.3}Sb_{0.3}O_n/SiO_2$ (45 wt %) | 2.7 | 1 | 0 | 4.2 | 4.5 | 5.2 |

Notes for Tables 1 and 2:
[*1]$H_2C_2O_4$Nb: Oxalic acid/niobium molar ratio with respect to aqueous niobium-oxalic acid solution (B)
$H_2O_2$/Sb: Hydrogen peroxide/antimony molar ratio with respect to the oxidation treatment of aqueous mixture (A)
$H_2O_2$/Nb: Hydrogen peroxide/niobium molar ratio with respect to aqueous niobium-oxalic acid solution (B)
[*2]The reaction conditions for the catalytic ammoxidation of propane in the gaseous phase are as follows. Composition of the gaseous feedstock mixture: [propane:ammonia:molecular oxygen:helium] molar ratio = 1:0.7:1.7:5.3  Reaction temperature: 420° C.

EXAMPLE 12

(Ammoxidation of Propane)

30 g of the oxide catalyst obtained in Example 1 was charged into a Vycor glass fluidized-bed reaction tube having an inner diameter of 25 mm. A gaseous feedstock mixture having a molar ratio of propane:ammonia:molecular oxygen:helium of 1:0.70:1.68:5.32 was fed into the reaction tube at a flow rate of 420 (ml/min). The reaction temperature was 440° C. (internal temperature), the reaction pressure was 0.049 MPa in terms of the gauge pressure, and the contact time was 2.4 (g·sec/ml).

24 Hours, 240 hours, 400 hours and 1000 hours after the start of the reaction, the produced gaseous reaction mixture was analyzed by means of an on-line gas chromatography apparatus. The results are shown in Table 3.

EXAMPLE 13

The ammoxidation reaction of propane was performed in substantially the same manner as in Example 12, except that 30 g of the oxide catalyst obtained in Example 1 was changed to 25 g of the oxide catalyst obtained in Example 11, the flow rate (F) of the gaseous feedstock mixture was changed from 420 (ml/min) to 460 (ml/min) and the contact time was changed from 2.4 (g·sec/ml) to 1.8 (g·sec/ml). The results are shown in Table 3.

As apparent from the results of Examples 12 and 13, by the use of the oxide catalyst of the present invention, even in the continuous catalytic ammoxidation of propane in the gaseous phase using a gaseous feedstock mixture having a high partial pressure of propane, the selectivity for the desired product (i.e., acrylonitrile) is maintained at a high level for a long time.

COMPARATIVE EXAMPLE 8

The ammoxidation reaction of propane was performed in substantially the same manner as in Example 12, except that 30 g of the oxide catalyst obtained in Example 1 was changed to 30 g of the oxide catalyst obtained in the Comparative Example 1 (which exhibits, in the ammoxidation reaction of propane, the highest selectivity for acrylonitrile among the oxide catalysts obtained in Comparative Examples)) and the contact time was changed from 2.4 (g sec/ml) to 2.8 (g sec/ml).

Since the oxide catalyst used was found to be deteriorated with the lapse of time, the flow rate (F) of the gaseous feedstock mixture was appropriately controlled such that the conversion of propane was maintained at approximately 50%. 240 Hours after the start of the reaction, the flow rate was 380 (ml/min). 400 Hours after the start of the reaction, the flow rate was 360 (ml/min).

However, since the selectivity for acrylonitrile was markedly lowered, the reaction was terminated 400 hours after the start of the reaction. The results are shown in Table 3.

TABLE 3

| | | Ammoxidation of propane[*1] | | | | | | | |
|---|---|---|---|---|---|---|---|---|---|
| | | 24 hours after the start of the reaction | | 240 hours after the start of the reaction | | 400 hours after the start of the reaction | | 1000 hours after the start of the reaction | |
| | Composition | Conversion of propane (%) | Selectivity for acrylo-nitrile (%) | Conversion of propane (%) | Selectivity for acrylo-nitrile (%) | Conversion of propane (%) | Selectivity for acrylo-nitrile (%) | Conversion of acrylo-propane (%) | Selectivity for nitrile (%) |
| Ex. 12 | $Mo_1V_{0.23}Sb_{0.26}Nb_{0.09}O_n$/ $SiO_2$ (45 wt %) | 50.2 | 60.1 | 50.0 | 59.6 | 50.0 | 59.7 | 49.9 | 59.7 |
| Ex. 13 | $Mo_1V_{0.23}Sb_{0.26}Nb_{0.09}O_n$/ $SiO_2$ (45 wt %) | 50.1 | 61.8 | 50.2 | 61.4 | 50.0 | 61.4 | 49.8 | 61.4 |
| Comp. Ex. 8 | $Mo_1V_{0.30}Sb_{0.23}Nb_{0.07}O_n$/ $SiO_2$(45 wt %) | 50.0 | 57.6 | 50.0 | 54.5 | 50.0 | 52.7 | | |

Notes:
[*1]The reaction conditions for the catalytic ammoxidation of propane in the gaseous phase are as follows.
Composition of the gaseous feedstock mixture: [propane:ammonia:molecular oxygen:helium] molar ratio = 1:0.7:1.68:5.32    Reaction temperature: 440° C.

EXAMPLE 14

(Preparation of a Catalyst)

An oxide catalyst represented by the formula: $Mo_1V_{0.23}Sb_{0.26}Nb_{0.09}O_n$/$SiO_2$(41% by weight) was prepared as follows.

Preparation of an oxide catalyst was performed in substantially the same manner as in Example 1, except that the amount of the silica sol was changed from 829 g to 704 g.

The composition of the oxide catalyst and the important conditions in the catalyst production process are shown in Table 4.

The obtained oxide catalyst exhibits, in an XRD pattern thereof, peaks at diffraction angles (2θ) of 7.8±0.3°, 8.9±0.3°, 22.1±0.3°, 27.1±0.3°, 28.1±0.3°, 35.2±0.3°, 36.1±0.3° and 45.2±0.3°, wherein R=0.08.

(Oxidation of Propane)

0.35 g of the obtained oxide catalyst (W=0.35 g) was charged into a fixed-bed type reaction tube having an inner diameter of 4 mm. A gaseous feedstock mixture having a molar ratio of propane:molecular oxygen:steam:helium of 1:3:14:10 was fed into the reaction tube at a flow rate (F) of 4.5 (ml/min). The reaction temperature (T) was 380° C. (external temperature) and the reaction pressure (P) was 0 MPa in terms of the gauge pressure. The contact time was 2.0 (g·sec/ml).

The produced gaseous reaction mixture was analyzed by means of a gas chromatography apparatus. The results are shown in Table 4.

COMPARATIVE EXAMPLE 9

(Preparation of a Catalyst)

An oxide catalyst represented by the formula: $Mo_1V_{0.30}Sb_{0.23}Nb_{0.07}O_n/SiO_2$ (41% by weight) was prepared as follows.

Preparation of an oxide catalyst was performed in substantially the same manner as in Comparative Example 1, except that the amount of the silica sol was changed from 829 g to 702 g.

The composition of the oxide catalyst and the important conditions in the catalyst production process are shown in Table 4.

The obtained oxide catalyst exhibited, in an XRD pattern thereof, peaks at diffraction angles (2θ) of 7.8±0.3°, 8.9±0.3°, 22.1±0.3°, 27.1±0.3°, 28.1±0.3°, 35.2±0.3°, 36.1±0.3° and 45.2±0.3°, wherein R=0.18.

(Oxidation of Propane)

Using the obtained oxide catalyst, the oxidation of propane was performed in substantially the same manner as in Example 14. The results are shown in Table 4.

TABLE 4

| | | Conditions of the catalyst production process[*1] | | | | Ammoxidation of propane[*2] | |
|---|---|---|---|---|---|---|---|
| | Composition | $H_2C_2O_4/$ Nb | $H_2O_2/$ Sb | $H_2O_2/$ Nb | Contact time (S) | Conversion of propane (%) | Selectivity for acrylo- nitrile (%) |
| Ex. 14 | $Mo_1V_{0.23}Sb_{0.26}Nb_{0.09}O_n/SiO_2$ (41 wt %) | 2.7 | 1 | 0 | 2.0 | 63.8 | 51.5 |
| Com. Ex. 9 | $Mo_1V_{0.30}Sb_{0.23}Nb_{0.07}O_n/SiO_2$ (41 wt %) | 2.7 | 1 | 0 | 2.0 | 63.5 | 48.1 |

Notes:
[*1]$H_2C_2O_4$/Nb: Oxalic acid/niobium molar ratio with respect to aqueous niobium-oxalic acid solution (B)
$H_2O_2$/Sb: Hydrogen peroxide/antimony molar ratio with respect to the oxidation treatment of aqueous mixture (A)
$H_2O_2$/Nb: Hydrogen peroxide/niobium molar ratio with respect to aqueous niobium-oxalic acid solution (B)
[*2]The reaction conditions for the catalytic oxidation of propane in the gaseous phase are as follows.
Composition of the gaseous feedstock mixture: [propane:molecular oxygen:steam:helium] molar ratio = 1:3:14:10  Reaction temperature: 380° C.

INDUSTRIAL APPLICABILITY

By the use of the oxide catalyst of the present invention in the oxidation or ammoxidation of propane or isobutane in the gaseous phase, (meth)acrylonitrile or (meth)acrylic acid can be produced with high selectivity and such high selectivity can be maintained for a long time, so that (meth)acrylonitrile or (meth)acrylic acid can be efficiently produced for a long time.

What is claimed is:

1. An oxide catalyst for use in catalytic oxidation or ammoxidation of propane or isobutane in the gaseous phase, which comprises a composition represented by the following formula (I):

$$Mo_1V_aSb_bNb_cZ_dO_n \quad (I)$$

wherein:
Z is at least one element selected from the group consisting of tungsten, chromium, titanium, aluminum, tantalum, zirconium, hafnium, manganese, iron, ruthenium, cobalt, rhodium, nickel, palladium, platinum, zinc, boron, indium, germanium, tin, lead, bismuth, yttrium, gallium, rare earth elements and alkaline earth metals; and a, b, c, d, and n are, respectively, the atomic ratios of vanadium (V), antimony (Sb), niobium (Nb), Z and oxygen (O), relative to molybdenum (Mo), wherein:
0.1≦a<0.4,
0.1<b≦0.4,
0.01≦c≦0.3,
0≦d≦1, with the proviso that a<b, and n is a number determined by and consistent with the valence requirements of the other elements present.

2. The oxide catalyst according to claim 1, wherein a in formula (I) satisfies the following relationship: 0.1≦a≦0.3.

3. The oxide catalyst according to claim 1, wherein b in formula (I) satisfies the following relationship: 0.1<b≦0.35.

4. The oxide catalyst according to claim 1, wherein c in formula (I) satisfies the following relationship: 0.05≦c≦0.2.

5. The oxide catalyst according to claim 1, wherein a in formula (I) satisfies the following relationship: 0.15≦a≦0.28.

6. The oxide catalyst according to claim 1, wherein b in formula (I) satisfies the following relationship: 0.2≦b≦0.33.

7. The oxide catalyst according to claim 1, wherein c in formula (I) satisfies the following relationship: 0.05≦c≦0.15.

8. The oxide catalyst according to claim 1, wherein a, b and c in formula (I) satisfy the following relationships:
0.15≦a≦0.28;
0.2≦b≦0.33;
0.05≦c≦0.15;
0.5≦a+b+c≦0.69;

$$\frac{a}{a+b+c} \geq 0.23; \text{ and}$$

$$0.59 - \frac{0.528a}{a+b+c} \leq \frac{b}{a+b+c} \leq 0.7 - \frac{0.524a}{a+b+c}.$$

9. The oxide catalyst according to claim 1, wherein a, b and c in formula (I) satisfy the following relationships:
0.16≦a≦0.28;
0.24≦b≦0.33;
0.07≦c≦0.15;
0.53≦a+b+c≦0.67;

$$\frac{a}{a+b+c} \geq 0.26; \text{ and}$$

$$0.63 - \frac{0.549a}{a+b+c} \leq \frac{b}{a+b+c} \leq 0.68 - \frac{0.529a}{a+b+c}.$$

10. The oxide catalyst according to claim 1, wherein a, b and c in formula (I) satisfy the following relationships:
$0.16 \leq a \leq 0.26$;
$0.24 \leq b \leq 0.30$;
$0.08 \leq c \leq 0.12$;
$0.57 \leq a+b+c \leq 0.60$;

$$\frac{a}{a+b+c} \geq 0.28; \text{ and}$$

$$0.67 - \frac{0.5975a}{a+b+c} \leq \frac{b}{a+b+c} \leq 0.67 - \frac{0.5352a}{a+b+c}.$$

11. The oxide catalyst according to claim 1, which exhibits, in an X-ray diffraction pattern thereof obtained using $CuK_\alpha$ as a source of X-ray, peaks at diffraction angles (2θ) of:
  22.1±0.3°, 28.1±0.3°, 36.1±0.3° and 45.2±0.3°;
  7.8±0.3°, 8.9±0.3°, 22.1±0.3°, 27.1±0.3°, 35.2±0.3° and 45.2±0.3°; or
  7.8±0.3°, 8.9±0.3°, 22.1±0.3°, 27.1±0.3°, 28.1±0.3°, 35.2±0.3°, 36.1±0.3° and 45.2±0.3°.

12. The oxide catalyst according to claim 1, which further comprises a silica carrier having supported thereon said oxide catalyst, wherein said silica carrier is present in an amount of from 20 to 60% by weight in terms of $SiO_2$, based on the total weight of said oxide catalyst and said silica carrier in terms of $SiO_2$.

13. The oxide catalyst according to claim 1, wherein Z in formula (I) is at least one element selected from the group consisting of tungsten, chromium, titanium, aluminum, tantalum, zirconium, iron, boron, indium, germanium and tin.

14. The oxide catalyst according to claim 1, which is produced by a method comprising providing an aqueous raw material mixture containing compounds of molybdenum, vanadium, antimony, niobium and optionally Z, and drying said aqueous raw material mixture, followed by calcination.

15. The oxide catalyst according to claim 14, wherein the calcination is performed at 500 to 700° C. in an atmosphere of inert gas which is substantially free of molecular oxygen.

16. The oxide catalyst according to claim 14, wherein said aqueous raw material mixture further contains oxalic acid, wherein the molar ratio of said oxalic acid to said niobium compound in terms of niobium is in the range of from 1 to 10.

17. A process for producing the oxide catalyst of claim 1, which comprises:
  providing an aqueous raw material mixture containing compounds of molybdenum, vanadium, antimony, niobium and optionally Z respectively in amounts which are adapted for producing an oxide catalyst comprising a composition represented by formula (I), and
  drying said aqueous raw material mixture, followed by calcination,
  thereby obtaining the oxide catalyst of claim 1.

18. The process according to claim 17, wherein the calcination is performed at 500 to 700° C. in an atmosphere of inert gas which is substantially free of molecular oxygen.

19. The process according to claim 17, wherein said aqueous raw material mixture further contains oxalic acid, wherein the molar ratio of said oxalic acid to said niobium compound in terms of niobium is in the range of from 1 to 10.

20. The oxide catalyst according to claim 1, wherein d in formula (I) satisfies the following relationship: $0 \leq d \leq 0.4$.

* * * * *